United States Patent [19]
Kucherlapati et al.

[11] Patent Number: 6,075,181
[45] Date of Patent: *Jun. 13, 2000

[54] HUMAN ANTIBODIES DERIVED FROM IMMUNIZED XENOMICE

[75] Inventors: Raju Kucherlapati, Darien, Conn.; Aya Jakobovits, Menlo Park, Calif.; Sue Klapholz, Stanford, Calif.; Daniel G. Brenner, San Mateo, Calif.; Daniel J. Capon, Hillsborough, Calif.

[73] Assignee: Abgenix, Inc., Fremont, Calif.

[*] Notice: This patent is subject to a terminal disclaimer.

[21] Appl. No.: 08/486,857

[22] Filed: Jun. 7, 1995

Related U.S. Application Data

[60] Division of application No. 08/430,938, Apr. 27, 1995, abandoned, which is a continuation-in-part of application No. 08/234,145, Apr. 28, 1994, abandoned, which is a continuation-in-part of application No. 08/112,848, Aug. 27, 1993, abandoned, which is a continuation-in-part of application No. 07/919,297, Jul. 24, 1992, abandoned, which is a continuation-in-part of application No. 07/610,515, Nov. 8, 1990, abandoned, which is a continuation-in-part of application No. 07/466,008, Jan. 12, 1990, abandoned.

[51] Int. Cl.$^7$ .......................... A61K 48/00; C12N 15/09; C12N 5/10

[52] U.S. Cl. ................. 800/25; 800/21; 800/18; 800/4; 800/6

[58] Field of Search .................. 800/2, 21, 18, 800/4, 6, 25; 424/184.1; 435/172.3, 240.2

[56] References Cited

U.S. PATENT DOCUMENTS

| | | | |
|---|---|---|---|
| 4,950,599 | 8/1990 | Bertling | 435/456 |
| 4,959,313 | 9/1990 | Taketo | 435/69.1 |
| 5,204,244 | 4/1993 | Fell et al. | 435/68 |
| 5,545,806 | 8/1996 | Lonberg et al. | 800/2 |
| 5,545,807 | 8/1996 | Surani et al. | 800/2 |
| 5,569,824 | 10/1996 | Donehower et al. | 800/2 |
| 5,569,825 | 10/1996 | Lonberg et al. | 800/18 |
| 5,591,669 | 1/1997 | Krimpenfort et al. | 800/2 |

FOREIGN PATENT DOCUMENTS

| | | | |
|---|---|---|---|
| 0 298 807 A1 | 6/1988 | European Pat. Off. | |
| 0 315 062 B1 | 5/1989 | European Pat. Off. | |
| 0 322 240 B1 | 6/1989 | European Pat. Off. | |
| 0 459 372 A3 | 5/1991 | European Pat. Off. | |
| 0 463 151 B1 | 1/1992 | European Pat. Off. | |
| WO 90/04036 | 4/1990 | WIPO . | |
| WO 91/00906 | 1/1991 | WIPO . | |
| WO 91/10741 | 7/1991 | WIPO . | |
| WO 92/03918 | 3/1992 | WIPO . | |
| WO 93/05165 | 3/1993 | WIPO | C12N 15/00 |
| WO 94/00569 | 1/1994 | WIPO | C12N 5/00 |
| WO 94/02602 | 2/1994 | WIPO . | |

OTHER PUBLICATIONS

Cox Dedoration for 07/990, 860 (5,545,806) Sep. 30, 1997.
Dorfman, Nickolas A., 1985, "The Optimal Technological Approach to the Development of Human Hybridomas," *Journal of Biological Response Modifiers* 4:213–239.
Taggart et al., 1983, "Stable Antibody–Producing Murine Hybridomas," *Science* 219:1228–1230.
Albertson, et al., "Construction and characterization of a yeast artificial chromosome library containing seven haploid human genome equivalents," *Proc. Natl. Acad. Sci. U.S.A.* 87:4256–4260 (1990).
Ayares, et al., "Sequence homology requirements for intermolecular recombination in mammalian cells," *Proc. Natl. Acad. Sci. U.S.A.* 83:5199–5203 (1986).
Berman, et al., "Content and organization of the human Ig $V_n$ locus: definition of three new $V_n$ families and linkage to the Ig $C_n$ locus" *EMBO J* 7:727–738 (1988).
Blankenstein, et al., "Immunoglobulin $V_n$ region genes of the mouse are organized in overlapping clusters" *Eur. J. Immunol.* 17:1351–1357 (1987).
Brinster, et al., "Introns increase transcriptional efficiency in transgenic mice," *Proc. Natl. Acad. Sci. U.S.A.* 85:836–840 (1988).
Brownstein, et al., "Isolation of single–copy human genes from a library of yeast artificial chromosomes", *Science* 244:1348–1351 (1989).
Bruggemann, et al., "Construction, function and immunogenicity of recombinant monoclonal antibodies," *Behring Inst. Mitt.* 87:21–24 (1990).
Bruggemann, et al , "Human antibody production in transgenic mice: expression from 100 kb of the human IgH locus," *Eur. J. Immunolog.* 21.1323–1326 (1991).
Bruggemann, et al., "A repertoire of monoclonal antibodies with human heavy chains from transgenic mice," *Proc. Natl. Acad. Sci. U.S.A.* 86:6709–6713 (1989).
Burke, et al., "Cloning of large segments of exogenous DNA into yeast by means of artificial chromosome vectors," *Science* 236:806–812 (1987).
Buttin, et al., "Exogenous Ig rearrangement in transgenic mice: a new strategy for human monoclonal antibody production," *Trends in Genetics* 3(8):205–206 (1987).
Davies, et al., 1992, "Targeted alterations in yeast artificial chromosomes for inter–species gene transfer," *Nucleic Acids Res.* 20:2693–2698 (1992).
Dorfman, N.A. "The optimal technological approach to the development of human hybridomas," *Journal of Biological Response Modifiers* 4:213–239 (1986).
Eliceiri, et al., "Stable integration and expression in mouse cells of yeast artificial chromosomes harboring human genes," *Proc. Natl. Acad. Sci. U.S.A.* 88:2179–2183 (1991).
Garza, et al., "Mapping the drosophilia genome with yeast artificial chromosomes with yeast artificial chromosomes", *Science* 246.641–646 (1989).

(List continued on next page.)

*Primary Examiner*—Karen M. Hauda
*Attorney, Agent, or Firm*—Fish & Neave; James F. Haley, Jr.; Jane T. Gunnison

[57] ABSTRACT

Antibodies with fully human variable regions against a specific antigen can be prepared by administering the antigen to a transgenic animal which has been modified to produce such antibodies in response to antigenic challenge, but whose endogenous loci have been disabled. Various subsequent manipulations can be performed to obtain either antibodies per se or analogs thereof.

3 Claims, 17 Drawing Sheets

OTHER PUBLICATIONS

Gnirke, et al., "Cloning and in vivo expression of the human GART gene using yeast artificial chromosomes", *EMBO Journal* 10(7):1629–16–14 (1991).

Huxley, et al., "The human HPRT gene on a yeast artificial chromosome is functional when transferred to mouse cells by cell fusion," *Genomics* 9:742–750 (1991).

Joyner, et al., "Production of a mutation in mouse En–2 gene by homologous recombination in embryonic stem cells," *Nature* 338:153–155 (1989).

Koller, et al., "Inactivating the β2–microglobulin locus in mouse embryonic stem cells by homologous recombination" *Proc. Nat'l. Acad. Sci.* 86:8932–8935 (1989).

Kucherlapati, R., "Homologous recombination in mammalian somatic cells," *Prog. Nucleic Acids Res. Mol. Biol* 36:301–310 (1989).

Matsuda, et al., "Structure and physical map of 64 variable segments in the 3'0.8– megabase region of the human immunoglobulin heavy chain locus," *Nature Genetics* 3:88–94 (1993).

Mortensen, et al., "Production of homozygous mutant ES cells with a single targeting construct," *Mol. Cell. Biol.* 12(5):2391–2395 (1991).

Pachnis, et al., "Transfer of a yeast artificial chromosome carrying human DNA from *Saccharomyces cerevisiae* into mammalian cells," *Proc. Natl. Acad. Sci. U.S.A.* 87:5109–5113 (1990).

Pavan, et al., "Modification and transfer into an embryonal carcinoma cell line of a 360–kilobase human–derived yeast artificial chromosome," *Mol. Cell. Biol.* 10(8):4163–4169 (1990).

Sakano, et al., "Identification and nucleotide sequence of a diversity DNA segment (D) of immunoglobulin heavy chain genes," *Nature* 290:562–565 (1981).

Shimizu, et al., "Immunoglobulin double–isotype expression by trans–mRNA in a human immunoglobulin transgenic mouse," *Proc. Natl. Acad. Sci. U.S.A.* 86:8020–8023 (1989).

Shin, et al., "Physical map of the 3' region of the human immunoglobulin heavy chain locus clustering of autoantibody–related variable segments in one haplotype," *EMBO* 10:3641–3645 (1991).

Taggart, et al., "Stable antibody–producing murine hybridomas," *Science* 219:1228–1230 (1983).

Thomas, et al., "Site–directed mutagenesis by gene targeting in mouse embryo–derived stem cells," *Cell* 51: 503–512 (1987).

Traver, et al., "Rapid screening of a human genomic library in yeast artificial chromosomes for single–copy sequences," *Proc. Natl. Acad. Sci. U.S.A.* 86:5898–5902 (1989).

Tucker, et al., "Mouse IgA heavy chain gene sequence: implications for evolution of immunoglobulin hinge exons," *Proc. Natl. Acad. Sci. U.S.A.* 78:7684–7688 (1981).

Yamamura, et al., "Cell–type specific and regulated expression of a human γ1 heavy–chain immunoglobulin gene in transgenic mice", *Proc. Natl. Acad. Sci. U.S.A.* 83:2152–2156 (1986).

Yancoupoulos and Alt. *Cell* 40:271–281 (1985).

Zachau, The human immunoglobulin κ locus and some of its acrobatics, *Biol. Chem.* 371. 1–6 (1990).

Aldhous, "Transgenic mice display a class (switching) act," *Science* 262:1212–1213 (1993).

Berman, et al., "Content and organization of the human Ig $V_H$ locus: definition of three new $V_H$ families and linkage to the Ig $C_H$ locus," *EMBO Journal* 7(3):727–738 (1988).

Bruggemann, et al., "A repertoire of monoclonal antibodies with human heavy chains from transgenic mice," *Proc. Natl. Acad. Sci USA* 86:6709–6713 (1989).

Choi, et al., "RNA splicing generates a variant light chain from an aberrantly rearranged κ gene," *Nature* 286.776–779 (1980).

Choi, et al., "Transgenic mice containing a human heavy chain immunoglobulin gene fragment cloned in a yeast artificial chromosome," *Nature Genetics* 4:117–123 (1993).

Jakobovits, et al., "Germ–line transmission and expression of a human–derived yeast artificial chromosome," *Nature* 362:255–258 (1993).

Joyner, et al., "Production of a mutation in mouse En–2 gene by homologous recombination in embryonic stem cells," *Nature* 338:153–156 (1989).

Max, et al., "Sequences of five potential recombination sites encoded close to an immunoglobulin κ constant region gene," *Proc. Natl. Acad. Sci. USA* 76(7):3450–3454 (1979).

Miller, et al., "Structural alterations in J regions of mouse immunoglobulin λ genes are associated with differential gene expression," *Nature* 295:428–430 (1982).

Morrison, S. "Success is in the Specification," *Nature,* 369, pp. 812–813 (1994).

Orkin, et al., "Mutation in an intervening sequence splice junction in man," *Proc. Natl. Acad. Sci. USA* 78(8):5041–5045 (1981).

Rajewsky, et al., "Evolutionary and somatic selection of the antibody repertoire in the mouse," *Science* 238:1088–1094 (1987).

Ramirez–Solis, et al., "Chromosome engineering in mice," *Nature* 378:720–724 (1995).

Sakano, et al., "Sequences at the somatic recombination sites of immunoglobulin light–chain genes," *Nature* 280:288–294 (1979).

Sakano, et al., "Two types of somatic recombination are necessary for the generation of complete immunoglobulin heavy–chain genes," *Nature* 286:676–683 (1980).

Schedl, et al., "A method for the generation of YAC transgenic mice by pronuclear microinjection," *Nucleic Acids Research* 21(20):4783–4787 (1993).

Schedl, et al., "A yeast artificial chromosome covering the tyrosinase gene confers copy number–dependent expression in transgenic mice," *Nature* 362:258–261 (1993).

Seidman, et al., "A Mutant immunoglobulin light chain is formed by aberrant DNA– and RNA–splicing events," *Nature* 286:779–783 (1980).

Shimizu, et al., "Immunoglobulin double–isotype expression by trans–mRNA in a human immunoglobulin transgenic mouse," *Proc. Natl. Acad. Sci. USA* 86:8020–8023 (1989).

Strauss, et al , "Germ line transmission of a yeast artificial chromosome spanning the murine $\alpha_1$ (1) collagen locus," *Science* 259. 1904–1907 (1993).

Capecchi et al., "Altering The Genome By Homologous Recombination," (1989) 244:1288–92.

Doetschman et al , "Targeted Mutation Of The HPRT Gene In Mouse Embryonic Stem Cells," (1988) 85:8583–8587.

Johnson et al., "Targeting Of Nonexpressed Genes In Embryonic Stem Cells Via Homologous Recombination," (1989) 245:1234–1236.

Mansour et al., "Disruption of the Proto–oncogene Int–2 Mouse Embryo–derived Stem Cells: A General Strategy For Targeting Mutations To Non–selectable Genes," (1988) 336:348–352.

Schedl et al , "Transgenic Mice Generated By Pronuclear Injection Of A Yeast Artificial Chromosome," (1992) 20:3073–3077.

Schwartzberg et al., "Germ–line Transmission Of A c–abl Mutation Produced By Targeted Gene Disruption In ES Cells," (1989) 246:799–803.

Treisman et al., "Specific Transcription and RNA Splicing Defects in Five Cloned β–Thalassaemia Genes," (1983) 302:591–596.

Zjilstra et al., "Germ–line Transmission Of A Disrupted β2–Microglobulin Gene Produced By Homologous Recombination in Embryonic Stem Cells," (1989) 342:435–438.

Green, L.L. et al., "Antigen–specific human monoclonal antibodies from mice engineered with human Ig heavy and light chain YACs," *Nat. Genet.* 7, pp. 13–21 (1994).

Emery, S.C. and Adair, J.R., "Humanised monoclonal Antibodies for Therapeutic Applications," *Expert Opinion on Investigation Drugs,* 3, pp. 241–251 (1994).

Herman N. Eisen, *Immunology:An Introduction to Molecular and Cellular Principles of the Immune Responses* 349–351 (2d ed. 1989).

James, K. and G.T.Bell, "Human Monoclonal Antibody Production: Current Status and Future Prospects," *J. Immunol. Methods,* 100, pp. 5–40 (1987).

Lenz et al., "Expression of Heterobispecific Antibodies By Genes Transfected Into Producer Hybridoma Cells," *Gene,* 87, pp. 213–218 (1990).

FIG. 17

```
                            CDR1
                            ↓
Germline B3       AACTACTTAG CTTGGTACCA GCAGAAACCA GGACAGCCTC CTAAGCTGCT  50
Hybridoma K4.1    AACTACTTAG CTTGGTACCA ACAGAAACCA GGACAGCCTC CTAAACTGCT  50
Germline JK4                                       ↑
                           ↑            CDR2           B3

Germline B3       CATTTACTGG GCATCTACCC GGGAATCCGG GGTCCCTGAC CGATTCAGTG  100
Hybridoma K4.1    CATTTACTGG GCATCTACCC GGGAATCCGG GGTCCCTGAC CGATTCAGTG  100
Germline JK4                                                              
                              ↑                               B3

Germline B3       GCAGCGGGTC TGGGACAGAT TTCACTCTCA CCATCAGCAG CCTGCAGGCT  150
Hybridoma K4.1    GCAGCGGGGTC TGGGACAGAT TTCACTCTCA CCATCAGCAG CCTGCAGGCT  150
Germline JK4                                                              
                                                                B3

Germline B3       GAAGATGTGG CAGTTTATTA CTGTCAGCAA TATTATAGT- TTCCGCTCAC  191
Hybridoma K4.1    GAAGATGTGG CACTTTATTA CTGTCAGCAA TATTATAGTC -GCTCAC     200
Germline JK4                                                              6
                                                                ↑
                                                      B3       J 4

Germline B3       TTTCGGCGGA GGGACCAAGG TGGAGATCAA ACGAACTGTG GCTGCACCAT  197
Hybridoma K4.1    TTTCGGCGGA GGGACCAAGG TGGAGATCAA AC-------- ----------  250
Germline JK4                                                              38
                             JK4                           ↑
                                                           hk Germline B3       CTGTCTTCAT CTTCCCGCCA TCTGATGAGC AGTTGAAATC TGGATACTGC  197
Hybridoma K4.1    ---------- ---------- ---------- ---------- ----------  300
Germline JK4                                                              38
                                         hk Germline B3       CTCTGTGTGT TGCCTGCTGA ATAACTTCTA TCCCAGAGAG GCCAAAGTAC  197
Hybridoma K4.1    ---------- ---------- ---------- ---------- ----------  350
Germline JK4                                                              38
                                         hk Germline B3       A
Hybridoma K4.1    -
GErmline JK4      
                  hk
```

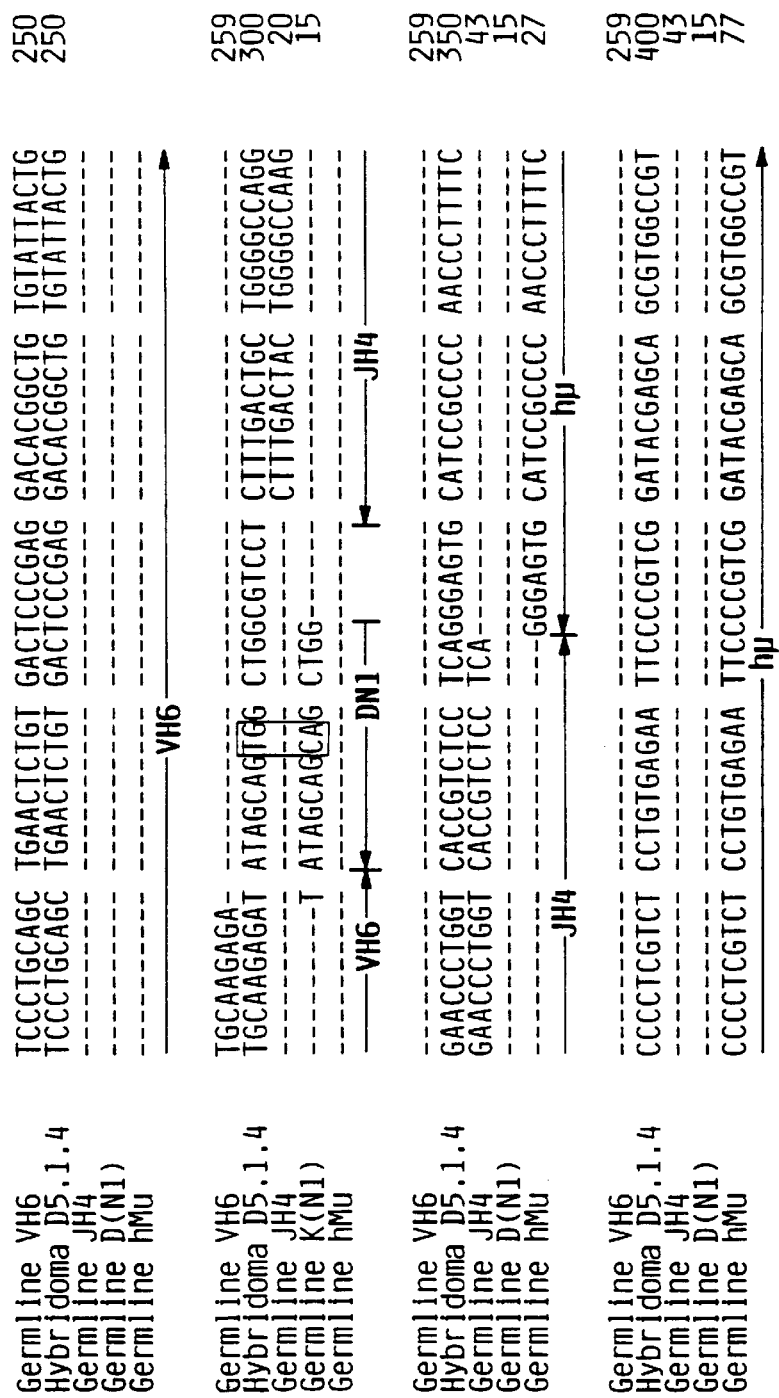

FIG. 19B

HUMAN ANTIBODIES DERIVED FROM IMMUNIZED XENOMICE

RELATED U.S. APPLICATION DATA

This application is a divisional of United States application Ser. No. 08/430,938, filed Apr. 27, 1995, now abandoned which is a continuation-in-part of United States application Ser. No. 08/234,145, filed Apr. 28, 1994, now abandoned, which is a continuation-in-part of United States application Ser. No. 08/112,848, filed Aug. 27, 1993, now abandoned, which is a continuation-in-part of United States application Ser. No. 07/919,297, filed Jul. 24, 1992, now abandoned, which is a continuation-in-part of United States application Ser. No. 07/610,515, filed Nov. 8, 1990, now abandoned, which is a continuation-in-part of United States application Ser. No. 07/466,008, filed Jan. 12, 1990, now abandoned.

TECHNICAL FIELD

The invention relates to the field of immunology, and in particular to the production of antibodies. More specifically, it concerns producing such antibodies by a process which includes the step of immunizing a transgenic animal with an antigen to which antibodies are desired. The transgenic animal has been modified so as to produce human, as opposed to endogenous antibodies.

BACKGROUND ART

PCT application WO 94/02602, published Feb. 3, 1994 and incorporated herein by reference, describes in detail the production of transgenic nonhuman animals which are modified so as to produce antibodies with fully human variable regions rather than endogenous antibodies in response to antigenic challenge. Briefly, the endogenous loci encoding the light and heavy immunoglobulin chains are incapacitated in the transgenic hosts and loci encoding human heavy and light chain proteins are inserted into the genome. In general, the animal which provides all the desired modifications is obtained by cross-breeding intermediate animals containing fewer than the full complement of modifications. The preferred embodiment of the nonhuman animal described in the specification is a mouse. Thus, mice, specifically, are described which, when administered immunogens, produce antibodies with human variable regions, including fully human antibodies, rather than murine antibodies that are immunospecific for these antigens.

The availability of such transgenic animals makes possible new approaches to the production of fully human antibodies. Antibodies with various immunospecificities are desirable for therapeutic and diagnostic use. Those antibodies intended for human therapeutic and in vivo diagnostic use, in particular, have been problematic because prior art sources for such antibodies resulted in immunoglobulins bearing the characteristic structures of antibodies produced by nonhuman hosts. Such antibodies tend to be immunogenic when used in humans.

The availability of the nonhuman, immunogen-responsive transgenic animals described in the above-referenced WO 94/02602 make possible convenient production of human antibodies without the necessity of employing human hosts.

DISCLOSURE OF THE INVENTION

The invention is directed to methods to produce human antibodies by a process wherein at least one step of the process includes immunizing a transgenic nonhuman animal with the desired antigen. The modified animal fails to produce endogenous antibodies, but instead produces B-cells which secrete immunoglobulins with fully human variable regions. The antibodies produced include fully human antibodies and can be obtained from the animal directly, or from immortalized B-cells derived from the animal. Alternatively, the genes encoding the immunoglobulins with human variable regions can be recovered and expressed to obtain the antibodies directly or modified to obtain analogs of antibodies such as, for example, single chain $F_V$ molecules.

Thus, in one aspect, the invention is directed to a method to produce an immunoglobulin with a fully human variable region to a specific antigen or to produce an analog of said immunoglobulin by a process which comprises immunizing a nonhuman animal with the antigen under conditions that stimulate an immune response. The nonhuman animal is characterized by being substantially incapable of producing endogenous heavy or light immunoglobulin chain, but capable of producing immunoglobulins either with both human variable regions and constant regions or with fully human variable regions or both. In the resulting immune response, the animal produces B cells which secrete immunoglobulins, with at least variable regions that are fully human, specific for the antigen. The human immunoglobulin of desired specificity can be directly recovered from the animal, for example, from the serum, or primary B cells can be obtained from the animal and immortalized. The immortalized B cells can be used directly as the source of human antibodies or, alternatively, the genes encoding the antibodies can be prepared from the immortalized B cells or from primary B cells of the blood or lymphoid tissue (spleen, tonsils, lymph nodes, bone marrow) of the immunized animal and expressed in recombinant hosts, with or without modification, to produce the immunoglobulin or its analogs. In addition, the genes encoding the repertoire of immunoglobulins produced by the immunized animal can be used to generate a library of immunoglobulins to permit screening for those variable regions which provide the desired affinity. Clones from the library which have the desired characteristics can then be used as a source of nucleotide sequences encoding the desired variable regions for further manipulation to generate antibodies or analogs with these characteristics using standard recombinant techniques.

In another aspect, the invention relates to an immortalized nonhuman B cell line derived from the above described animal. In still another aspect, the invention is directed to a recombinant host cell-which is modified to contain the gene encoding either the human immunoglobulin with the desired specificity, or an analog thereof which exhibits the same specificity.

In still other aspects, the invention is directed to antibodies or antibody analogs prepared by the above described methods and to recombinant materials for their production.

In still other aspects, the invention is directed to antibodies with fully human variable regions, including fully human antibodies which are immunospecific with respect to particular antigens set forth herein and to analogs which are similarly immunospecific, as well as to the recombinant materials useful in the production of these antibodies.

BRIEF DESCRIPTION OF THE DRAWINGS

FIG. 12A shows the separation of human activated T cells into CD4+ and CD4− populations. Panel B shows the results of a FACS analysis of the activated CD4+T cells with antibodies from the xenomouse immunized with gp39 which contain murine heavy chain γ constant regions; panel C shows the corresponding results with respect to CD4− populations.

FIG. 17 shows the complete nucleotide sequence of the light chain from the antibody secreted by K4.1.

FIGS. 18A–18B show the complete nucleotide sequence of the heavy chain from the antibody secreted by D5.1.

FIGS. 19A–19B show the complete nucleotide sequence of the light chain from the antibody secreted by D5.1.

MODES OF CARRYING OUT THE INVENTION

Figure 1:
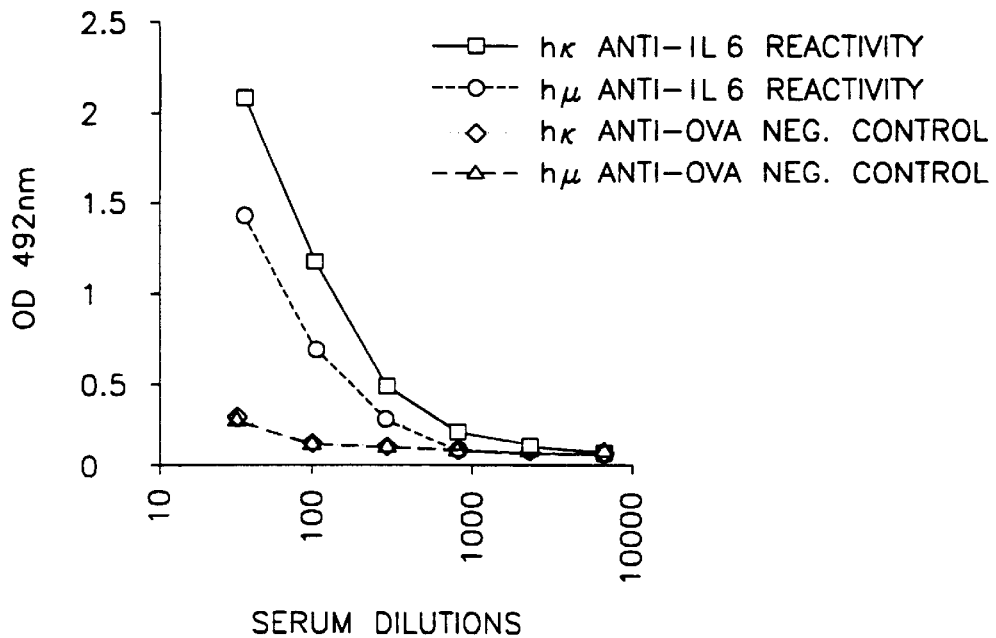
FIG. 1 shows the serum titers of anti-IL-6 antibodies from a xenomouse immunized with human IL-6 and which antibodies contain human kappa light chains and/or human μ heavy chains.

In general, the methods of the invention include administering an antigen for which human forms of immunospecific reagents are desired to a transgenic nonhuman animal which has been modified genetically so as to be capable of producing human, but not endogenous, antibodies. Typically, the animal has been modified to disable the endogenous heavy and/or light chain loci in its genome, so that these endogenous loci are incapable of the rearrangement required to generate genes encoding immunoglobulins in response to an antigen. In addition, the animal will have been provided, stably, in its genome, at least one human heavy chain locus and at least one human light chain locus so that in response to an administered antigen, the human loci can rearrange to provide genes encoding human immunoglobulins immunospecific for the antigen.

The details for constructing such an animal useful in the method of the invention are provided in the PCT application WO 94/02602 referenced above.

For production of the desired antibodies, the first step is administration of the antigen. Techniques for such administration are conventional and involve suitable immunization protocols and formulations which will depend on the nature of the antigen per se. It may be necessary to provide the antigen with a carrier to enhance its immunogenicity and/or to include formulations which contain adjuvants and/or to administer multiple injections, and the like. Such techniques are standard and optimization of them will depend on the characteristics of the particular antigen for which immunospecific reagents are desired.

As used herein, the term "immunospecific reagents" includes immunoglobulins and their analogs. The term "analogs" has a specific meaning in this context. It refers to moieties that contain the fully human portions of the immunoglobulin which account for its immunospecificity. In particular, variable regions including the complementarity determining regions (CDRs) are required, along with sufficient portions of the framework regions (FRs) to result in the appropriate three dimensional conformation. Typical immunospecific analogs of antibodies include $F_{(ab')_2}$, $F_{ab'}$, and $F_{ab}$ regions. Modified forms of the variable regions to obtain, for example, single chain $F_V$ analogs with the appropriate immunospecificity are known. A review of such $F_V$ construction is found, for example, in *Tibtech* (1991) 9:. The construction of antibody analogs with multiple immunospecificities is also possible by coupling the human variable regions derived from antibodies with varying specificities.

The variable regions with fully human characteristics can also be coupled to a variety of additional substances which can provide toxicity, biological functionality, alternative binding specificities and the like. The moieties including the fully human variable regions produced by the methods of the invention include single-chain fusion proteins, molecules coupled by covalent methods other than those involving peptide linkages, and aggregated molecules. Examples of analogs which include variable regions coupled to additional molecules covalently or noncovalently include those in the following nonlimiting illustrative list. Traunecker, A. et al. *Int J Cancer Supp* (1992) *Supp* 7:51–52 describe the bispecific reagent janusin in which the $F_V$ region directed to CD3 is coupled to soluble CD4 or to other ligands such as OVCA and IL-7. Similarly, the fully human variable regions produced by the method of the invention can be constructed into $F_V$ molecules and coupled to alternative ligands such as those illustrated in the cited article. Higgins, P. J. et al. *J Infect Disease* (1992) 166:198–202 describe a heteroconjugate antibody composed of OKT3 cross-linked to an antibody directed to a specific sequence in the V3 region or GP120. Such heteroconjugate antibodies can also be constructed using at least the human variable regions contained in the immunoglobulins produced by the invention methods. Additional examples of bispecific antibodies include those described by Fanger, M. W. et al. *Cancer Treat Res.* (1993) 68: 181–194 and by Panger, M. W. et al. *Crit Rev Immunol* (1992) 12: 101–124. Conjugates that are immunotoxins including conventional antibodies have been widely described in the art. The toxins may be coupled to the antibodies by conventional coupling techniques or immunotoxins containing protein toxin portions can be produced as fusion proteins. The analogs of the present invention can be used in a corresponding way to obtain such immunotoxins. Illustrative of such immunotoxins are those described by Byrs, B. S. et al. *Seminars Cell Biol* (1991) 2:59–70 and by Fanger, M. W. et al. *Immunol Today* (1991) 12:51–54.

In short, the genes encoding the immunoglobulins produced by the transgenic animals of the invention can be retrieved and the nucleotide sequences encoding the fully human variable region can be manipulated according to known techniques to provide a variety of analogs such as those described above. In addition, the immunoglobulins themselves containing the human variable regions can be modified using standard coupling techniques to provide conjugates retaining immunospecificity and fully human characteristics in the immunospecific region.

Thus, immunoglobulin "analogs" refers to moieties which contain those portions of the antibodies or the invention which retain their human characteristics and their immunospecificity. These will retain sufficient human variable region to provide the desired specificity.

As stated above, all of the methods of the invention include administering the appropriate antigen to the transgenic animal. The recovery or production of the antibodies themselves can be achieved in various ways.

First, and most straightforward, the polyclonal antibodies produced by the animal and secreted into the bloodstream can be recovered using known techniques. Purified forms of these antibodies can, of course, be readily prepared by standard purification techniques, preferably including affinity chromatography with respect to the particular antigen, or even with respect to the particular epitope of the antigen for which specificity is desired. In any case, in order to monitor the success of immunization, the antibody levels with respect to the antigen in serum will be monitored using standard techniques such as ELISA, RIA and the like.

It will be noted, from the examples below, that a portion of the polyclonal antiserum obtained may include an endogenous heavy chain constant region derived from the host, even though the variable regions are fully human. Under these circumstances, to the extent that an application requires fully human antibodies, use of the polyclonal antiserum directly would be inappropriate. However, the presence of these chimeras, which is believed to result from in vivo isotype switching as described by Gerstein et al. *Cell* (1990) 63:537, is not problematic, in view of conventional purification and modification methods and in view of the availability of alternative methods to recover fully human antibodies, if desired, described in the following paragraphs.

First, and most simply, the polyclonal antiserum could be subjected to suitable separation techniques to provide compositions containing only fully human immunoglobulins. Portions of the serum which display characteristics of the host species can be removed, for example, using affinity reagents with the appropriate anti species immunoglobulins or immunospecific portions thereof. Furthermore, for applications where only the variable regions of the antibodies are required, treating the polyclonal antiserum with suitable reagents so as to generate $F_{ab}$, $F_{ab'}$, or $F_{(ab')_2}$ portions results in compositions containing fully human characteristics. Such fragments are sufficient for use, for example, in immunodiagnostic procedures involving coupling the immunospecific portions of immunoglobulins to detecting reagents such as radioisotopes. Thus, for some applications, the polyclonal antiserum can be treated to provide compositions with the desired characteristics including compositions consisting essentially of fully human antibodies and compositions including immunoglobulin analogs wherein the immunospecific portion is fully human.

Alternatively, immunoglobulins and analogs with desired characteristics can be generated from immortalized B cells derived from the transgenic animals used in the method of the invention or from the rearranged genes provided by these animals in response to immunization. It will be apparent that hybridomas derived from the B cells of the immunized animal can be screened so as to choose only those secreting fully human antibodies and that the genetic material can be recovered from the hybridomas or from lymphocytes in spleen, blood, or lymph nodes of the immunized animal and manipulated using conventional techniques to replace any endogenous constant region with a human one or to produce a desired analog.

Thus, as an alternative to harvesting the antibodies directly from the animal, the B cells can be obtained, typically from the spleen, but also, if desired, from the peripheral blood lymphocytes or lymph nodes and immortalized using any of a variety of techniques, most commonly using the fusion methods described by Kohler and Milstein. The resulting hybridomas (or otherwise immortalized B cells) can then be cultured as single colonies and screened for secretion of antibodies of the desired specificity. As described above, the screen can also include a determination of the fully human character of the antibody. For example, as described in the examples below, a sandwich ELISA wherein the monoclonal in the hybridoma supernatant is bound both to antigen and to an antihuman constant region can be employed. Conversely, hybridomas that secrete antibodies which are immunoreactive with antispecies antibodies directed to the species of the immunized animal can be discarded. After the appropriate hybridomas are selected, the desired antibodies can be recovered, again using conventional techniques. They can be prepared in quantity by culturing the immortalized B cells using conventional methods, either in vitro, or in vivo to produce ascites fluid. Purification of the resulting monoclonal antibody preparations is less burdensome than in the case of serum since each immortalized colony will secrete only a single type of antibody. In any event, standard purification techniques to isolate the antibody from other proteins in the culture medium can be employed.

As an alternative to obtaining human immunoglobulins directly from the culture of immortalized B cells derived from the animal, the immortalized cells can be used as a source of rearranged heavy chain and light chain loci for subsequent expression and/or genetic manipulation. Isolation of genes from such antibody-producing cells is straightforward since high levels of the appropriate mRNAs are available for production of a cDNA library. The recovered rearranged loci can be manipulated as desired. For example, the constant region can be exchanged for that of a different isotype or that of a human antibody, as described above, or eliminated altogether. The variable regions can be linked to encode single chain $F_V$ regions. Multiple $F_V$ regions can be linked to confer binding ability to more than one target or chimeric heavy and light chain combinations can be employed. Once the genetic material is available, design of analogs as described above which retain their ability to bind the desired target, as well as their human characteristics, is straightforward.

Once the appropriate genetic material is obtained and, if desired, modified to encode an analog, the coding sequences including those that encode, at a minimum, the variable regions of the human heavy and light chain can be inserted into expression systems contained on vectors which can be transfected into standard recombinant host cells. As described below, a variety of such host cells may be used; for efficient processing, however, mammalian cells are preferred. Typical mammalian cell lines useful for this purpose include CHO cells, 293 cells, or NSO-GS cells.

The production of the antibody or analog is then undertaken by culturing the modified recombinant host under culture conditions appropriate for the growth of the host cells and the expression of the coding sequences. The antibodies are then recovered from the culture. The expression systems are preferably designed to include signal peptides so that the resulting antibodies are secreted into the medium; however, intracellular production is also possible.

In addition to deliberate design of modified forms of the immunoglobulin genes to produce analogs, advantage can be taken of phage display techniques to provide libraries containing a repertoire of antibodies with varying affinities for the desired antigen. For production of such repertoires, it is unnecessary to immortalize the B cells from the immunized animal; rather the primary B cells can be used directly as a source of DNA. The mixture of cDNAs obtained from B cells, e.g., derived from spleens, is used to prepare an expression library, for example, a phage display library transfected into $E.\ coli$. The resulting cells are tested for immunoreactivity to the desired antigen. Techniques for the identification of high affinity human antibodies from such libraries are described by Griffiths, A. D., et al., $EMBO\ J$ (19.94) 13:3245–3260; by Nissim, A., et al. ibid, 692–698, and by Griffiths, A. D., et al., ibid, 725–734. Ultimately, clones from the library are identified which produce binding affinities of a desired magnitude for the antigen, and the DNA encoding the product responsible for such binding is recovered and manipulated for standard recombinant expression. Phage display libraries may also be constructed using previously manipulated nucleotide sequences and screened in similar fashion. In general, the cDNAs encoding heavy and light chain are independently supplied or are linked to form $F_V$ analogs for production in the phage library.

The phage library is thus screened for the antibodies with highest affinity for the antigen and the genetic material recovered from the appropriate clone. Further rounds of screening can increase the affinity of the original antibody isolated. The manipulations described above for recombinant production of the antibody or modification to form a desired analog can then be employed.

As above, the modified or unmodified rearranged loci are manipulated using standard recombinant techniques by constructing expression systems operable in a desired host cell, such as, typically, a Chinese hamster ovary cell, and the desired immunoglobulin or analog is produced using standard recombinant expression techniques, and recovered and purified using conventional methods.

The application of the foregoing processes to antibody production has enabled the preparation of human immunospecific reagents with respect to antigens for which human antibodies have not heretofore been available. The immunoglobulins that result from the above-described methods and the analogs made possible thereby, provide novel compositions for use in analysis, diagnosis, research, and therapy. The particular use will, of course, depend on the immunoglobulin or analog prepared. In general, the compositions of the invention will have utilities similar to those ascribable to nonhuman antibodies directed against the same antigen. Such utilities include, for example, use as a affinity ligands for purification, as reagents in immunoassays, as components of immunoconjugates, and as therapeutic agents for appropriate indications.

Particularly in the case of therapeutic agents or diagnostic agents for use in vivo, it is highly advantageous to employ antibodies or their analogs with fully human characteristics. These reagents avoid the undesired immune responses engendered by antibodies or analogs which have characteristics marking them as originating from non-human species. Other attempts to "humanize" antibodies do not result in reagents with fully human characteristics. For example, chimeric antibodies with murine variable regions and human constant regions are easily prepared, but, of course, retain murine characteristics in the variable regions. Even the much more difficult procedure of "humanizing" the variable regions by manipulating the genes encoding the amino acid sequences that form the framework regions does not provide the desired result since the CDRs, typically of nonhuman origin, cannot be manipulated without destroying immunospecificity. Thus, the methods of the present invention provide, for the first time, immunoglobulins that are fully human or analogs which contain immunospecific regions with fully human characteristics.

There are large numbers of antigens for which human antibodies and their human analogs would be made available by the methods of the invention. These include the following as a nonlimiting set:

leukocyte markers, such as CD2, CD3, CD4, CD5, CD6, CD7, CD8, CD11a,b,c, CD13, CD14, CD18, CD19, CD20, CD22, CD23, CD27 and its ligand, CD28 and its ligands B7.1, B7.2, B7.3, CD29 and its ligand, CD30 and its ligand, CD40 and its ligand gp39, CD44, CD45 and isoforms, CDw52 (Campath antigen), CD56, CD58, CD69, CD72, CTLA-4, LFA-1 and TCR histocompatibility antigens, such as MHC class I or II, the Lewis Y antigens, SLex, SLey, SLea, and SLeb;

integrins, such as VLA-1, VLA-2, VLA-3, VLA-4, VLA-5, VLA-6, and LFA-1;

adhesion molecules, such as Mac-1 and p150,95;

selectins, such as L-selectin, P-selectin, and E-selectin and their counterreceptors VCAM-1, ICAM-1, ICAM-2, and LFA-3;

interleukins, such as IL-1, IL-2, IL-3, IL-4, IL-5, IL-6, IL-7, IL-8, IL-10, IL-11, IL-12, IL-13, IL-14; and IL-15;

interleukin receptors, such as IL-1R, IL-2R, IL-4R, IL-5R, IL-6R, IL-7R, IL-8R, IL-10R, IL-11R, IL-12R, IL-13R, IL-14R, and IL-15R;

chemokines, such as PF4, RANTES, MIP1α, MCP1, NAP-2, Grou, Grog, and IL-8;

growth factors, such as TNFalpha, TGFbeta, TSH, VEGF/VPF, PTHrP, EGF family, FGF, PDGF family, endothelin, and gastrin releasing peptide (GRP);

growth factor receptors, such as TNFalphaR, RGFbetaR, TSHR, VEGFR/VPFR, FGFR, EGFR, PTHrPR, PDGFR family, EPO-R, GCSF-R and other hematopoietic receptors;

interferon receptors, such as IFNαR, IFNβR, and IFNγR;

Igs and their receptors, such as IgE, FceRI, and FCeRII;

tumor antigens, such as her2-neu, mucin, CEA and endosialin;

allergens, such as house dust mite antigen, lol p1 (grass) antigens, and urushiol;

viral proteins, such as CMV glycoproteins B, H, and gCIII, HIV-1 envelope glycoproteins, RSV envelope glycoproteins, HSV envelope glycoproteins, EBV envelope glycoproteins, VZV envelope glycoproteins, HPV envelope glycoproteins, Hepatitis family surface antigens;

toxins, such as pseudomonas endotoxin and osteopontin/uropontin, snake venom, and bee venom;

blood factors, such as complement C3b, complement C5a, complement C5b-9, Rh factor, fibrinogen, fibrin, and myelin associated growth inhibitor;

enzymes, such as cholesterol ester transfer protein, membrane bound matrix metalloproteases, and glutamic acid decarboxylase (GAD); and miscellaneous antigens including ganglioside GD3, ganglioside GM2, LMP1, LMP2, eosinophil major basic protein, eosinophil cationic protein, PANCA, Amadori protein, Type IV collagen, glycated lipids, γ-interferon, A7, P-glycoprotein and Fas (AFO-1) and oxidized-LDL.

Particularly preferred immunoglobulins and analogs are those immunospecific with respect to human IL-6, human IL-8, human TNFα, human CD4, human L-selectin, and human gp39. Human antibodies against IL-8 are particularly useful in preventing tumor metastasis and inflammatory states such as asthma. Antibodies and analogs immunoreactive with human TNFα and human IL-6 are useful in treating cachexia and septic shock as well as autoimmune disease. Antibodies and analogs immunoreactive with gp39 or with L-selectin are also effective in treating or preventing autoimmune disease. In addition, anti-gp39 is helpful in treating graft versus host disease, in preventing organ transplant rejection, and in treating glomerulonephritis. Antibodies and analogs against L-selectin are useful in treating ischemia associated with reperfusion injury.

Typical autoimmune diseases which can be treated using the above-mentioned antibodies and analogs include systemic lupus erythematosus, rheumatoid arthritis, psoriasis, Sjogren's, scleroderma, mixed connective tissue disease, dermatomyositis, polymyositis, Reiter's syndrome, Behcet's disease, Type 1 diabetes, Hashimoto's thyroiditis, Grave's disease, multiple sclerosis, myasthenia gravis and pemphigus.

The examples below are intended to illustrate but not to limit the invention.

In these examples, mice, designated "xenomice", are used for initial immunizations. A detailed description of such xenomice is found in the above referenced PCT application WO 94/02602. Immunization protocols appropriate to each antigen are described in the specific examples below. The sera of the immunized xenomice (or the supernatants from immortalized B cells) were titrated for antigen specific human antibodies in each case using a standard ELISA format. In this format, the antigen used for immunization was immobilized onto wells of microtiter plates. The plates were washed and blocked and the sera (or supernatants) were added as serial dilutions for 1–2 hours of incubation. After washing, bound antibody having human characteristics was detected by adding the appropriate antispecies Ig (typically antihuman kappa or antihuman μ) conjugated to horseradish peroxidase (HRP) for one hour. In some cases, the bound antibodies were tested for murine characteristics using antimurine antibodies, typically antimurine γ. After again washing, the chromogenic reagent o-phenylene diamine (OPD) substrate and hydrogen peroxide were added and the plates were read 30 minutes later at 492 nm using a microplate reader.

Unless otherwise noted, the antigen was coated using plate coating buffer (0.1 M carbonate buffer, pH 9.6); the assay blocking buffer used was 0.5% BSA, 0.1% Tween 20 and 0.01% Thimerosal in PBS; the substrate buffer used in color development was citric acid 7.14 g/l: dibasic sodium phosphate 17.96 g/l; the developing solution (made immediately before use) was 10 ml substrate buffer, 10 mg OPD, plus 5 ml hydrogen peroxide; the stop solution (used to stop color development) was 2 M sulfuric acid. The wash solution was 0.05% Tween 20 in PBS.

EXAMPLE 1

Human Antibodies Against Human IL-6

Three to 5 xenomice aged 8–20 weeks were age-matched and immunized intraperitoneally with 50 μg human IL-6 emulsified in complete Freund's adjuvant for primary immunization and in incomplete Freund's adjuvant for subsequent injections. The mice received 6 injections 2–3 weeks apart. Serum titers were determined after the second dose and following each dose thereafter. Bleeds were performed 6–7 days after injections from the retrobulbar plexus. The blood was allowed to clot at room temperature for about 2 hours and then incubated at 4° C. for at least 2 hours before separating and collecting the sera.

ELISAs were conducted as described above by applying 100 μl per well of recombinant human IL-6 at 2 mg/ml in coating buffer. Plates were then incubated at 4° C. overnight or at 37° C. for 2 hours and then washed three times in washing buffer. Addition of 100 μl/well blocking buffer was followed by incubation at room temperature for 2 hours, and an additional 3 washes.

Then, 50 μl/well of diluted serum samples (and positive and negative controls) were added to the plates. Plates were then incubated at room temperature for 2 hours and again washed 3 times.

After washing, 100 μl per well of either HRP-mouse antihuman IgM at 1/2,000 or HRP-mouse antihuman kappa at 1/2,000, diluted in blocking buffer were added. After a 1 hour incubation at room temperature, the plates were washed 3 times and developed with OPD substrate for 10–25 minutes. 50 μl/well of stop solution were then added and the results read on an ELISA plate reader at 492 nm. The dilution curves resulting from the titration of serum from xenomouse A40-7 after 6 injections are shown in FIG. 1. The data in FIG. 1 show production of anti-IL-6 immunoreactive with antihuman kappa and antihuman μ detectable at serum dilutions above 1:1,000.

EXAMPLE 2

Human Antibodies Against Human IL-8

Immunization and serum preparation were as described in Example 1 as except that human recombinant IL-8 was used as an immunogen.

Figure 2:
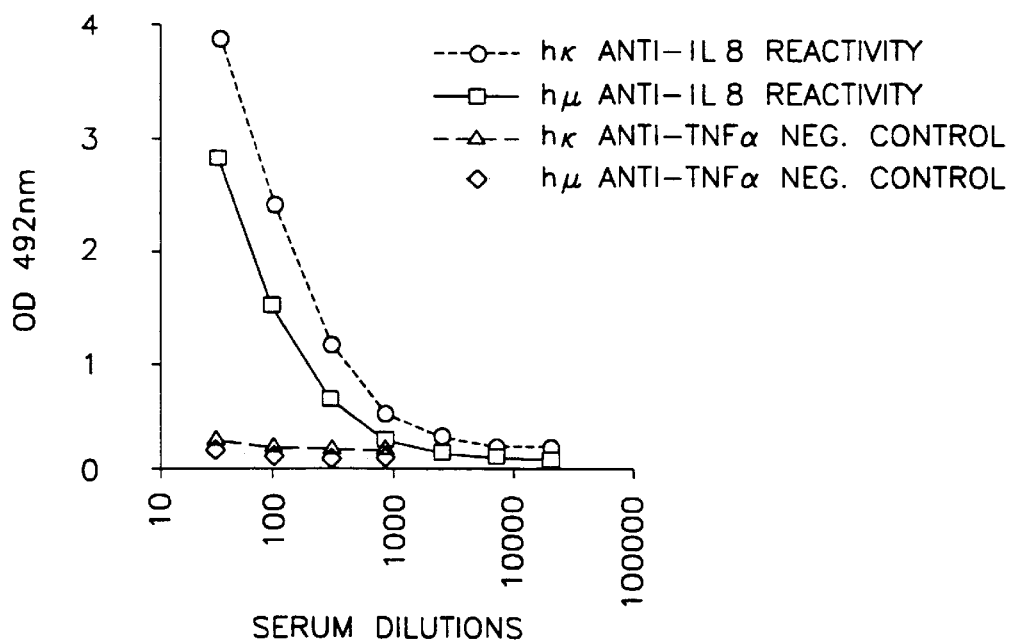
FIG. 2 shows the serum titers of anti-IL-8 antibodies from a xenomouse immunized with human IL-8 and which antibodies contain human kappa light chains and/or human μ heavy chains.

ELISA assays were performed with respect to the recovered serum, also exactly as described in Example 1, except that the ELISA plates were initially coated using 100 μl/well of recombinant human IL-8 at 0.5 mg/ml in the coating buffer. The results obtained for various serum dilutions from xenomouse A260-5 after 6 injections are shown in FIG. 2. Human anti-IL-8 reactivity was again shown at serum dilutions having concentrations higher than that represented by a 1:1,000 dilution.

EXAMPLE 3

Human Antibodies Against Human TNFα

Immunization and serum preparation were conducted as described in Example 1 except that human recombinant TNFα was substituted for human IL-6. ELISAs were conducted as described in Example 1 except that the initial coating of the ELISA plate employed 100 μl/well recombinant human TNFα at 1 mg/ml in coating buffer.

Figure 3:
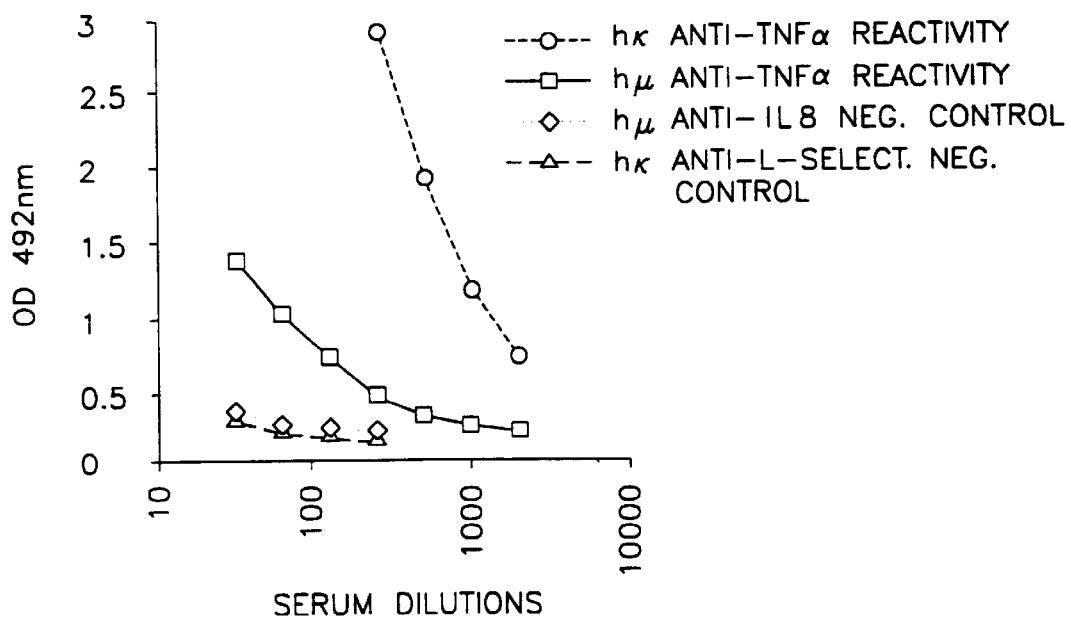
FIG. 3 shows the serum titers of anti-TNFα antibodies from a xenomouse immunized with human TNF-α and which antibodies contain human kappa light chains and/or human μ heavy chains.

The dilution curves for serum from xenomouse A210-8 after 6 injections obtained are shown in FIG. 3. Again significant titers of human anti-TNFα reactivity were shown.

EXAMPLE 4

Human Antibodies Against Human CD4

The human CD4 antigen was prepared as a surface protein on transfected recombinant cells as follows: Human CD4 zeta (F15 LTR) as described in Roberts, et al., *Blood* (1994) 84:2878 was introduced into the rat basophil leukemic cell line RBL-2H3, described by Callan, M., et al., *Proc Natl Acad Sci USA* (1993) 90:10454 using the kat high efficiency transduction system described by Finer, et al., *Blood* (1994) 83:43. Briefly, RBL-2H3 cells at $10^6$ cells per well were cultured in 750 ml. DMEM$^{low}$+20% FBS (Gibco) and 16 μg/ml polybrene with an equal volume of proviral supernatant for 2 hours at 37° C., 5% $CO_2$. One ml of medium was removed and 750 μl of infection medium and retroviral supernatant were added to each well and the cultures incubated overnight. The cells were washed and expanded in DMEM$^{low}$+10% FBS until sufficient cells were available for sorting. The CD4-zeta transduced RBL-2H3 cells were sorted using the FACSTAR plus (Becton Dickinson). The cells were stained for human CD4 with a mouse antihuman CD4-PE antibody and the top 2–3% expressing cells were selected.

Figure 4:
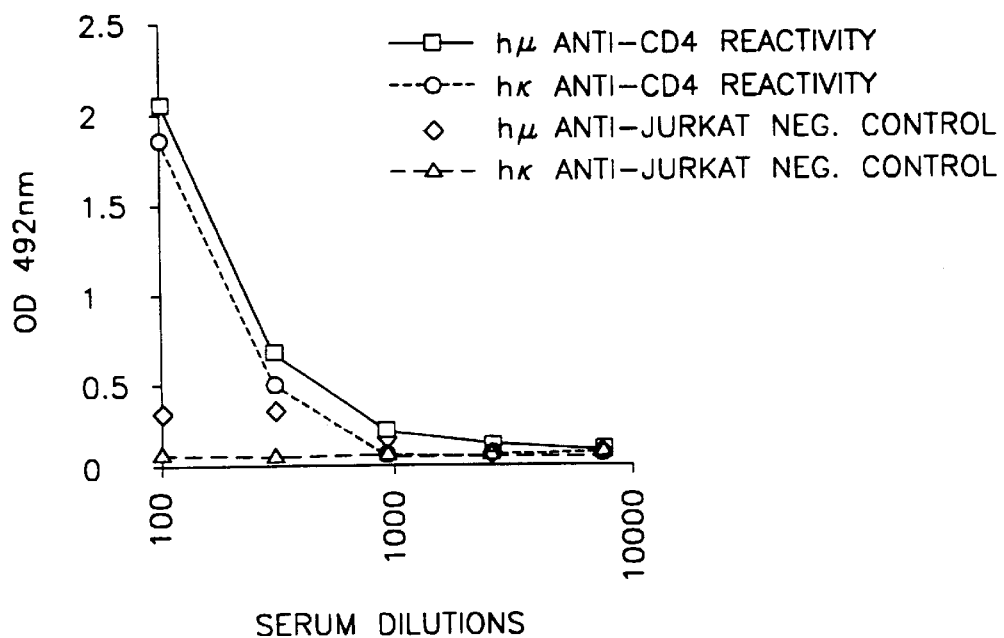
FIG. 4 shows the serum titers of anti-CD4 antibodies from a xenomouse immunized with human CD4 and which antibodies contain human kappa light chains and/or human μ heavy chains.

Immunizations were conducted as described in Example 1 using 10×$10^6$ cells per mouse except that the primary injection was subcutaneous at the base of the neck. The mice received 6 injections 2–3 weeks apart. Serum was prepared and analyzed by ELISA as described in Example 1 except that the initial coating of the ELISA plate utilized 100 μl per well of recombinant soluble CD4 at 2 mg/ml of coating buffer. The titration curve for serum from xenomouse A207-1 after 6 injections is shown in FIG. 4. Titers of human anti-CD4 reactivity were shown at concentrations representing greater than those at 1:1,000 dilution.

EXAMPLE 5

Human Antibodies Against Human L-Selectin

The antigen was prepared as a surface displayed protein in C51 cells, a high expressing clone derived by transfecting the mouse pre-B cell 300.19 with LAM-1 cDNA (LAM-1 is the gene encoding L-selectin) (Tedder, et al., *J Immunol* (1990) 144:532) or with similarly transfected CHO cells. The transfected cells were sorted using fluorescent activated cell sorting using anti-Leu-8 antibody as label.

The C51 and the transfected CHO cells were grown in DME 4.5 g/l glucose with 10% FCS and 1 mg/ml G418 in 100 mm dishes. Negative control cells, 3T3-P317 (transfected with gag/pol/env genes of Moloney virus) were grown in the same medium without G418.

Primary immunization was by injection subcutaneously at the base of the neck; subsequent injections were intraperitoneal. 70–100 million C51 or transfected CHO cells were used per injection for a total of five injections 2–3 weeks apart.

Sera were collected as described in Example 1 and analyzed by ELISA in a protocol similar to that set forth in Example 1.

For the ELISA, the transfected cells were plated into 96 well plates and cell monolayers grown for 1–2 days depending on cell number and used for ELISA when confluent. The cells were fixed by first washing with cold 1×PBS and then fixing solution (5% glacial acetic acid, 95% ethanol) was added. The plates were incubated at −25° C. for 5 minutes and can be stored at this temperature if sealed with plate sealers.

The ELISA is begun by bringing the plates to room temperature, flicking to remove fixing solution and washing 5 times with DMEM medium containing 10% FCS at 200 μl per well.

The wells were treated with various serum dilutions or with positive or negative controls. Positive control wells contained murine IgG1 to human L-selectin.

Figure 5:
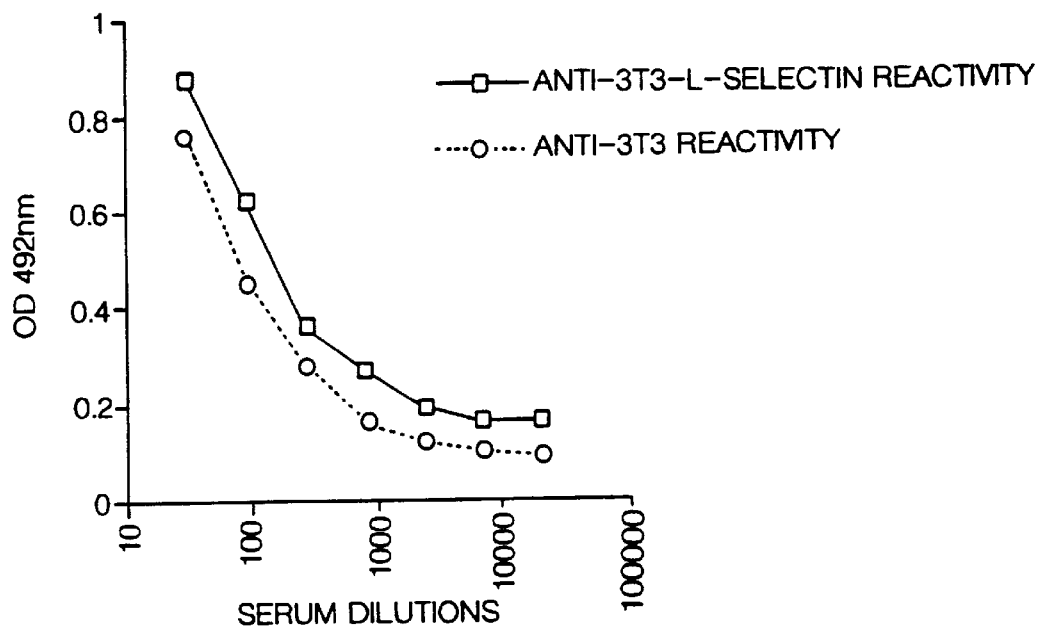
FIG. 5 shows the serum titers of a xenomouse immunized with 300.19 cells expressing L-selectin at their surface. In the ELISA assay used, these antibodies are detectable only if they carry human μ constant region heavy chains.
Figure 6:
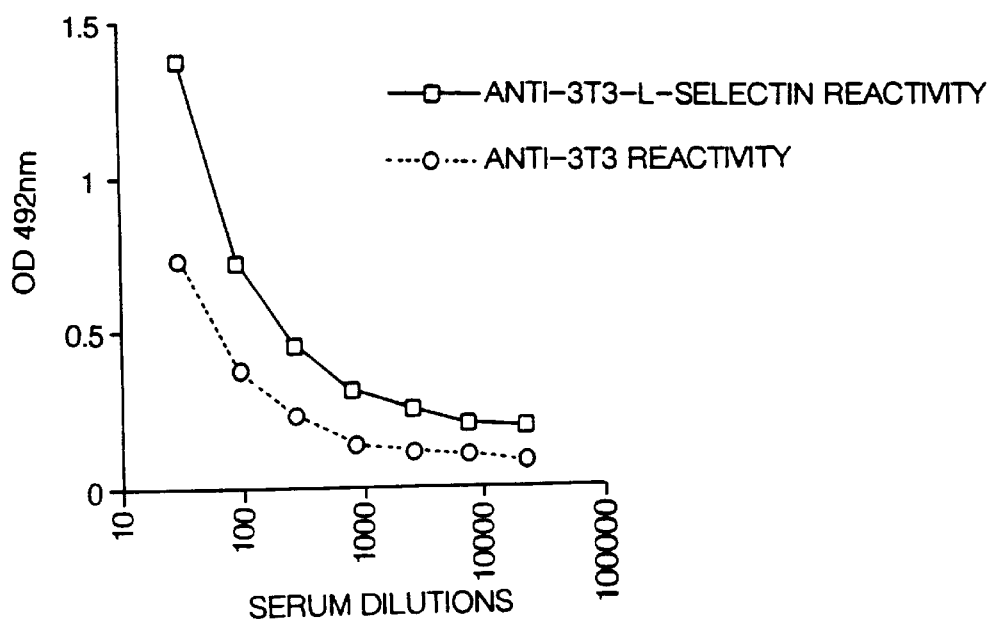
FIG. 6 shows the serum titers of a xenomouse immunized with 300.19 cells expressing L-selectin at their surface. In the ELISA assay used, these antibodies are detectable only if they carry human kappa light chains.

The wells were incubated for 45 minutes and monolayer integrity was checked under a microscope. The wells were then incubated with either HRP-antimouse IgG (1/1000) or with the antihuman kappa or antihuman μ conjugates described in Example 1. The plates were then washed with 1% BSA/PBS and again with PBS and monolayer integrity was checked. The plates were developed, stopped, and read as described above. The results for serum from xenomouse A303-3 are shown in FIGS. 5 and 6; human antibodies both to L-selectin and control 3T3 cells were obtained. However, the serum titers are higher for the L-selectin-expressing cells as compared to parental 3T3 cells. These results show that xenomouse A303-3 produces antibodies specific for L-selectin with human μ heavy chain regions and/or human kappa light chains.

ELISAs were also performed using as the immobilized antigen a fusion protein consisting of the extracellular domain of human L-selectin fused to the constant domain of human $IgG_1$ (Guo, et al., *Cell Immunol* (1994) 154:202). The L-selectin fusion protein was made by transient transfection of human 293 cells using calcium phosphate transfection (Wigler, M., *Cell* (1979) 16:777). Serum preparation was performed as described in Example 1. ELISAs were conducted essentially as in Example 1, except that the initial coating of the ELISA plate employed 100 μl transfected 293 cell culture supernatant containing the L-selectin-Ig fusion protein. Detection employed HRP-mouse antihuman kappa and HRP-goat antimouse IgG.

Figure 7:
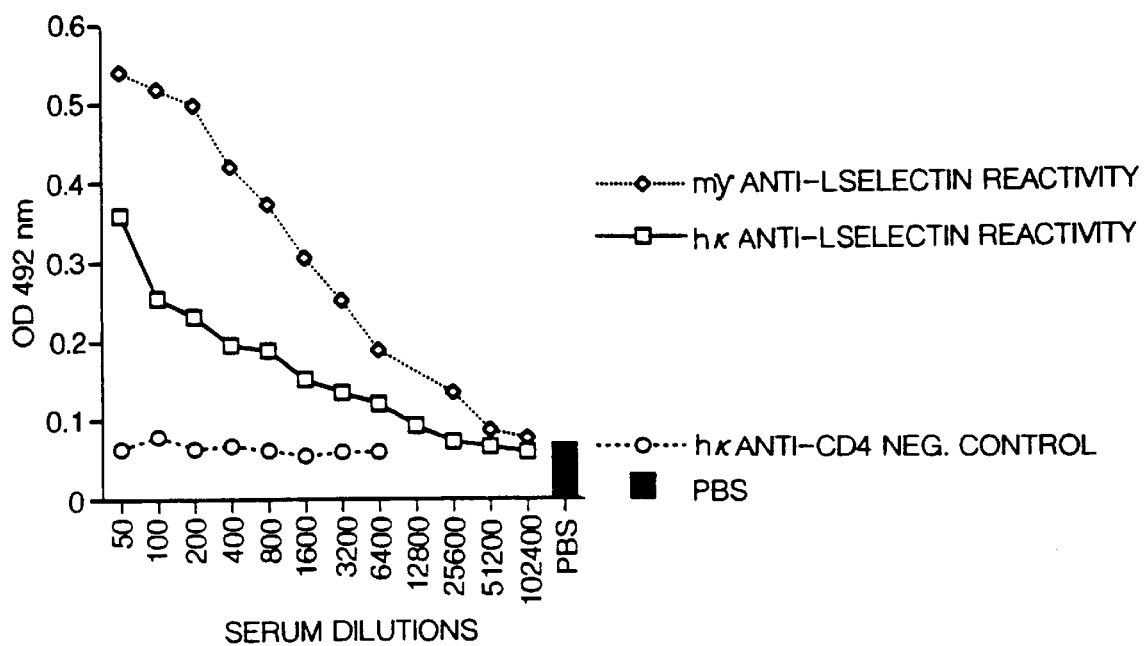
FIG. 7 shows the serum titers of a xenomouse immunized with 300.19 cells expressing L-selectin. In this ELISA, these antibodies are detectable if they carry human kappa light chain and/or murine γ constant regions.

FIG. 7 shows the results from xenomouse A195-2; antibodies specific for L-selectin having human kappa light chains and/or murine heavy chain γ regions are present in the serum.

The antisera obtained from the immunized xenomice were also tested for staining of human neutrophils. Human neutrophils were prepared as follows: peripheral blood was collected from normal volunteers with 100 units/ml heparin. About 3.5 ml blood was layered over an equal volume of One-step Polymorph Gradient (Accurate Chemical, Westbury, N.Y.) and spun for 30 minutes at 450×G at 20° C. The neutrophil fraction was removed and washed twice in DPBS/2% FBS.

The neutrophils were then stained with either:

(1) antiserum from xenomouse A195-2 immunized with C51 cells (expressing L-selectin);

(2) as a positive control, mouse monoclonal antibody LAM1-3 (against L-selectin); and (3) as negative control, antiserum from a xenomouse immunized with cells expressing human gp39.

Figure 8:
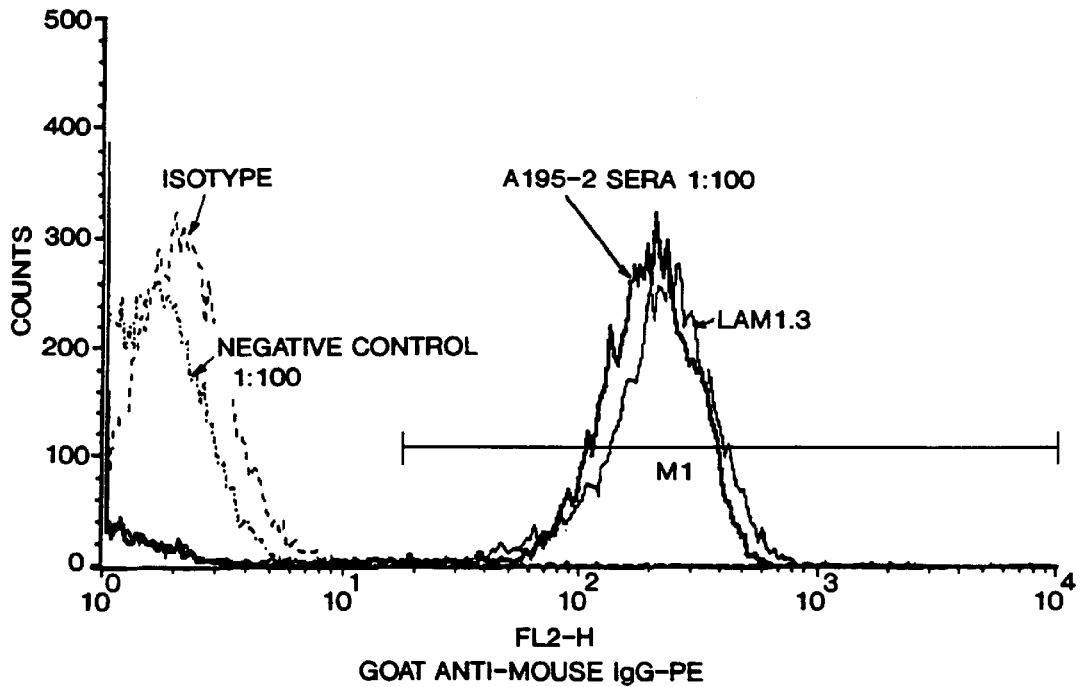
FIG. 8 shows a FACS analysis of human neutrophils coupled to sera from a xenomouse (A195-2) immunized with human L-selectin and labeled with an antibody immunoreactive with murine heavy chain γ constant region.
Figure 9:
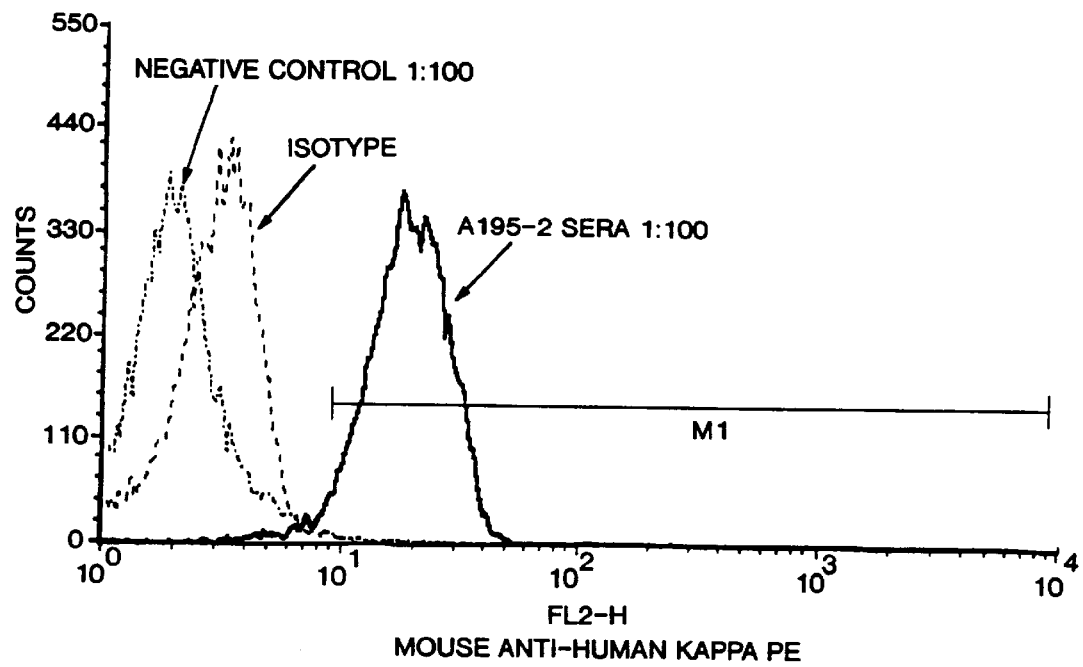
FIG. 9 shows a FACS analysis of human neutrophils incubated with serum from a xenomouse (A195-2) immunized with human L-selectin and labeled with an antibody immunoreactive with human light chain kappa region.

The stained, washed neutrophils were analyzed by FACS. The results for antiserum from xenomouse A195-2 are shown in FIGS. 8 and 9.

These results show the presence of antibodies in immunized xenomouse serum which contain fully human variable regions immunoreactive with L-selectin. The negative control antiserum from mice immunized with gp39 does not contain antibodies reactive against human neutrophils. Serum from A195-2 (immunized with L-selectin-expressing cells) contains antibodies binding to human neutrophils detectable with a goat antimouse IgG (FIG. 8), which immunoreacts with heavy chain protein composed of fully human variable regions and mouse γ constant regions. Staining with anti L-selectin xenomouse antisera detected with a mouse monoclonal antibody against human kappa is shown in FIG. 9, showing the presence of fully human kappa light chain.

As explained above, these antibodies containing human variable regions are readily convertible to fully human antibodies. For example, using hybridomas secreting these antibodies, the cDNAs encoding them can be obtained. By amplifying the genes encoding human V regions using primers containing restriction enzyme recognition sites and cloning them into plasmids containing the coding sequences for human constant regions as described by Queen, et al., *Proc Natl Acad Sci* (1989) 86:10029, genes encoding the fully human antibodies can be obtained for recombinant production.

EXAMPLE 6

Human Antibodies Against Human gp39 gp39 (the ligand for CD40) is expressed on activated human CD4+T cells. The sera of xenomice immunized with recombinant gp39 according to this example contained antibodies immunospecific for gp39 with fully human variable regions; the sera contained fully human IgM antibodies and chimeric IgG antibodies containing human variable regions and murine constant heavy chain γ region.

Figure 10:
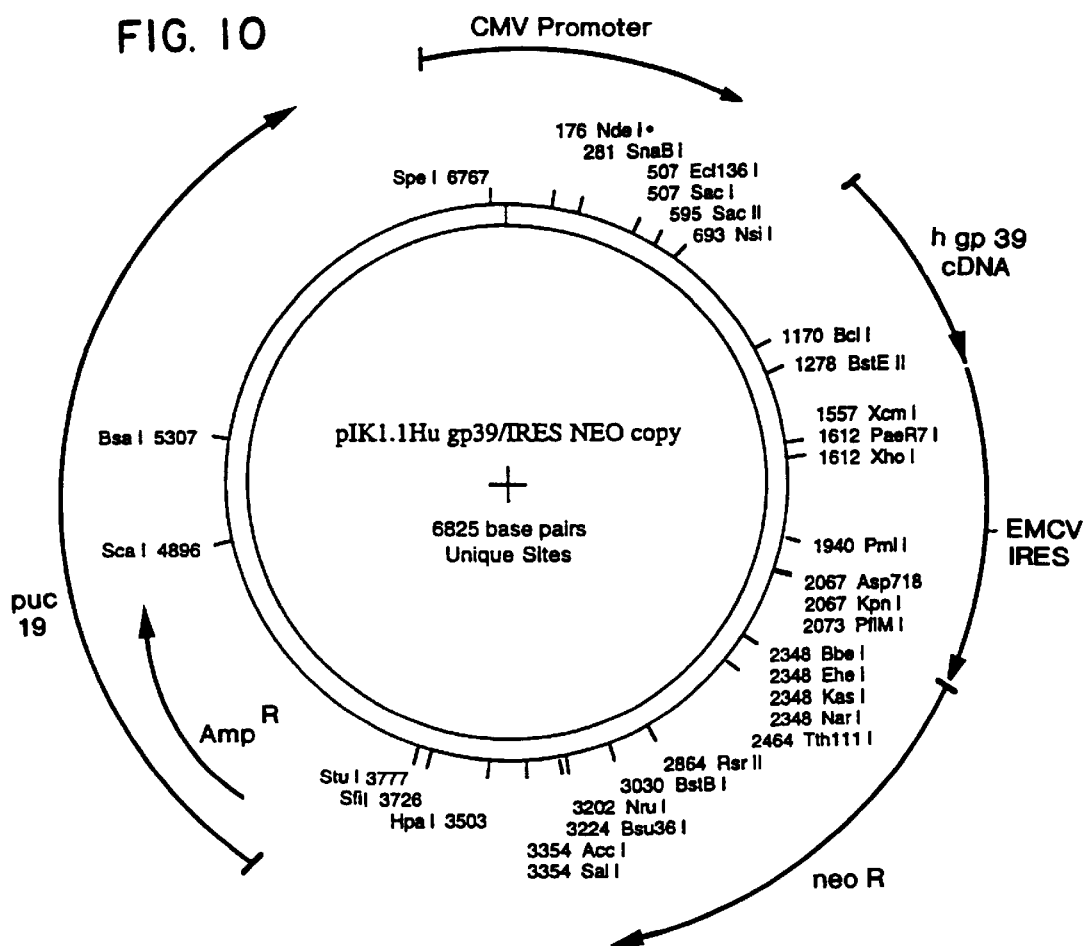
FIG. 10 is a diagram of a plasmid used to transfect mammalian cells to effect the production of the human protein gp39.

The antigen consisted of stable transfectants of 300.19 cells or of CHO cells expressing gp39 cDNA cloned into the mammalian expression vector P1K1.HUgp39/IRES NEO as shown in FIG. 10. CHO cells were split 1:10 prior to transfection in DMEM 4.5 g/l glucose, 10% FBS, 2 mM glutamine, MEM, NEAA supplemented with additional glycine, hypoxanthine and thymidine. The cells-were cotransfected with the gp39 vector at 9 μg/10 cm plate (6×10$^5$ cells) and the DHFR expressing vector pSV2DHFRs (Subranani et al. *Mol Cell Biol* (1981) a:854) at 1 μg/10 cm plate using calcium phosphate transfection. 24 hours later the cells were split 1:10 into the original medium containing G418 at 0.6 mg/ml. Cells producing gp39 were sorted by FACS using an anti-gp39 antibody.

Mice grouped as described in Example 1 were immunized with 300.19 cells expressing gp39 using a primary immunization subcutaneously at the base of the neck and with secondary intraperitoneal injections every 2–3 weeks. Sera were harvested as described in Example 1 for the ELISA assay. The ELISA procedure was conducted substantially as set forth in Example 1; the microtiter plates were coated with CHOD-gp39 cells grown in a 100 mm dish in DMEM, 4.5 g/l glucose, 10% FCS, 4 mM glutamine, and nonessential amino acid (NEAA) solution for MEM (100×). On the day preceding the ELISA assay, the cells were trypsinized and plated into 96-well filtration plates at 10$^5$ cells/200 μl well and incubated at 37° C. overnight. The positive controls were mouse antihuman gp39; negative controls were antisera from mice immunized with an antigen other than gp39. 50 μl of sample were used for each assay. The remainder of the assay is as described in Example 1.

Figure 11:
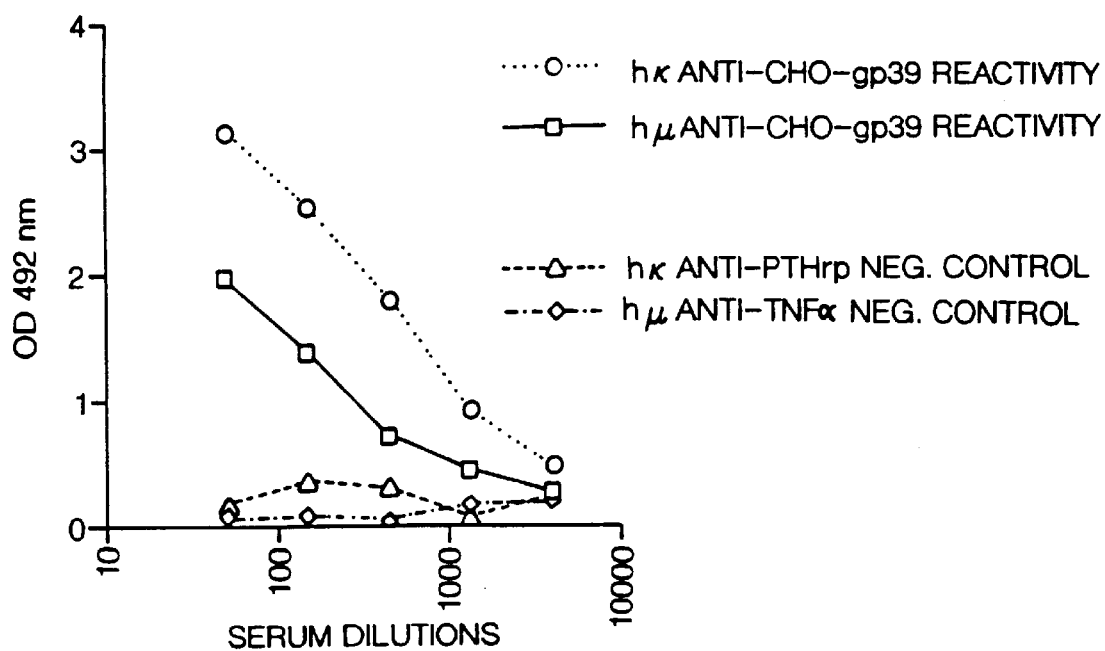
FIG. 11 represents the serum titration curve of mice immunized with CHO cells expressing human gp39. The antibodies detected in this ELISA must be immunoreactive with gp39 and contain human heavy chain μ constant regions or human kappa light chains.

The dilution curves for the sera obtained after 4 injections from mice immunized with gp39 expressed on CHO cells are shown in FIG. 11. As shown, the sera contained antihuman gp39 immunospecificity which is detectable with human kappa and human μ HRP-coupled antibodies.

In addition, the sera were tested for their ability to react with activated human T cells included in PBMC using FACS analysis. To prepare the PBMC, human peripheral blood was collected from normal volunteers with the addition of 100 unit/ml heparin. PBMC were isolated over Ficoll gradient and activated with 3 μg/ml PHA, 1 μg/ml PMA in IMDM plus 10% FBS plus 25 μM 2-mercaptoethanol for 4 hours. After washing, the PBMC were stained with mouse Mab against human CD4 labeled with FITC to permit separation of activated human T cells from unactivated cells.

The activated CD4+ and CD4– T cells were then analyzed by FACS using staining with either:

1) antiserum from a Xenomouse immunized with 300.19 cells producing gp39;

2) a positive control mouse Mab directed against α-CD40L (human gp39); and 3) a negative control antiserum from a Xenomouse immunized with TNF.

The detecting antibody in the FACS analysis was goat antimouse IgG (PE). The results are shown in FIG. 12.

Figure 12A:
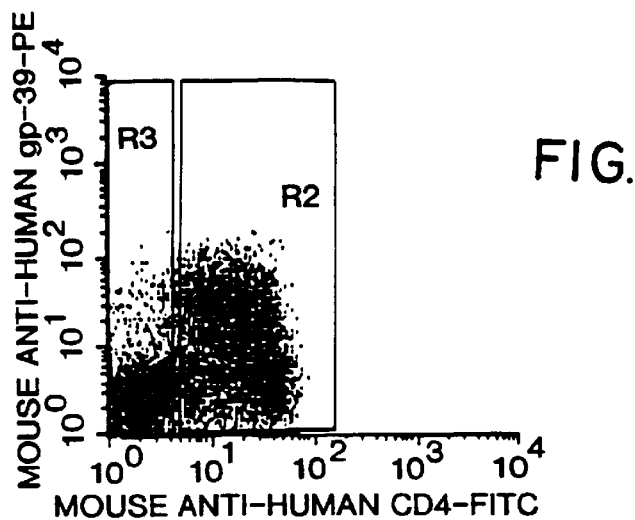
FIGS. 12A–C shows the results of a FACS analysis of antibodies from a xenomouse (labeled A247-4) immunized with human gp39 reacted with activated human T cells.
Figure 12B:
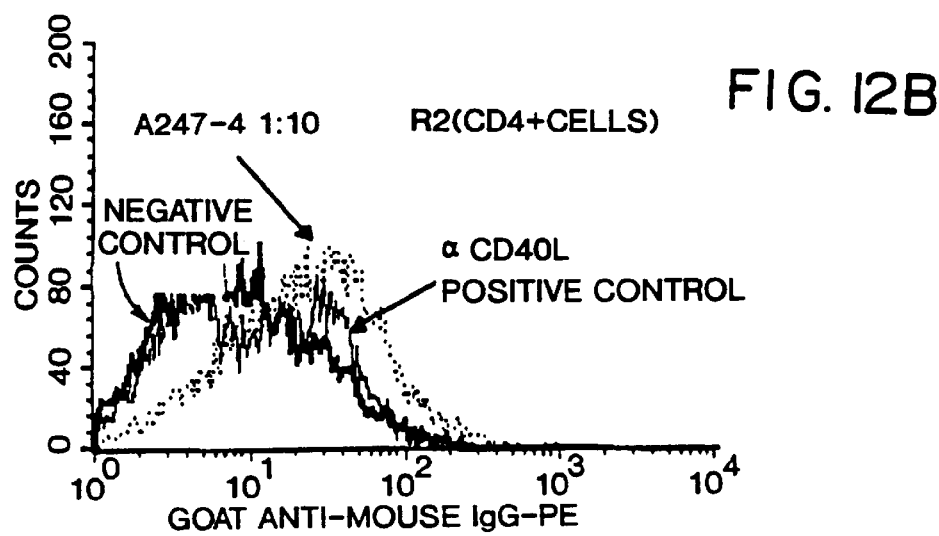
Figure 12C:
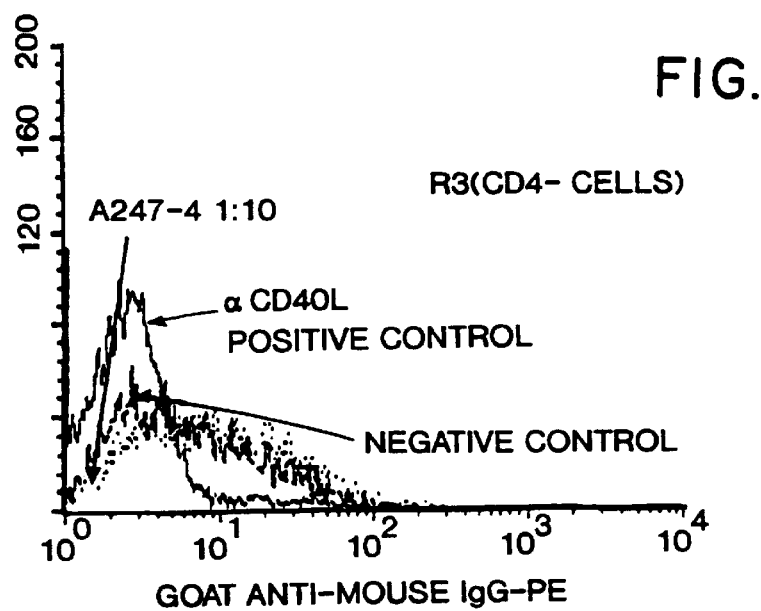

As shown in FIG. 12A, CD4+ (R2) and CD4– (R3) cells were separated prior to FACS analysis. Panel B shows the results for CD4+ cells and shows that sera from mice immunized with gp39 (labeled A247-4 in the figure) reacted with these activated PBMC; panel C shows that these sera did not react with CD4– cells. These antibodies carried immune heavy chain γ constant regions. The results of panels B and C confirm that the TNF-injected xenomouse did not make antibodies against activated human T cells.

EXAMPLE 7

Preparation of High-Affinity Human Mabs Against Tetanus Toxin

The antibodies prepared in this example were secreted by hybridomas obtained by immortalizing B cells from xenomice immunized with tetanus toxin. The immunization protocol was similar to that set forth in Example 1 using 50 μg tetanus toxin emulsified in complete Freund's adjuvant for intraperitoneal primary immunization followed by subsequent intraperitoneal injections with antigen incorporated into incomplete Freund's adjuvant. The mice received a total of 4 injections 2–3 weeks apart.

After acceptable serum titers of antitetanus toxinC (anti-TTC) were obtained, a final dose of antigen in PBS was given 4 days before the animals were sacrificed and the spleens harvested for fusion.

The spleen cells were fused with myeloma cells P3X63-Ag8.653 as described by Galfre, G. and Milstein, C. *Methods in Enzymology* (1981) 73:3–46.

After fusion the cells were resuspended in DMEM, 15% FCS, containing HAT supplemented with glutamine, pen/strep for culture at 37° C. and 10% $CO_2$. The cells were plated in microtiter trays and maintained in HAT-supplemented medium for two weeks before transfer to HT-supplemented media. Supernatants from wells containing hybridomas were collected for a primary screen using an ELISA.

The ELISA was conducted as described in Example 1 wherein the antigen coating consisted of 100 μl/well of tetanus toxin C (TTC) protein at 2 mg/ml in coating buffer, followed by incubation at 4° C. overnight or at 37° C. for two hours. In the primary ELISA, HRP-conjugated goat antimouse IgG at 1/2000 was used in addition to HRP mouse antihuman IgM as described in Example 1. Two hybridomas that secreted anti-TTC according to the ELISA assay, clone D5.1 and clone K4.1 were used for further analysis.

Figure 13:
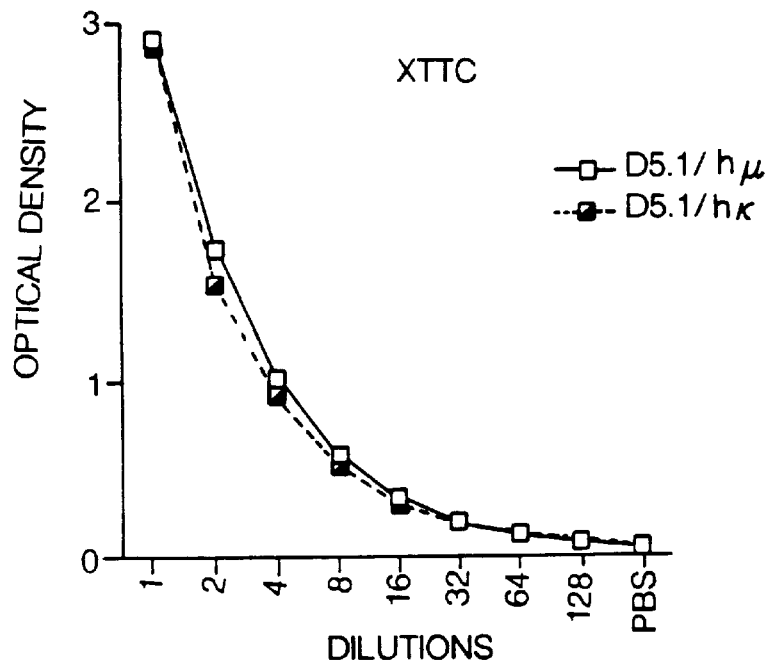
FIG. 13 is a titration curve with respect to monoclonal antibodies secreted by the hybridoma clone D5.1. This clone is obtained from a xenomouse immunized with tetanus toxin C (TTC) and contains human kappa light chain and human μ constant region in the heavy chain.
Figure 14:
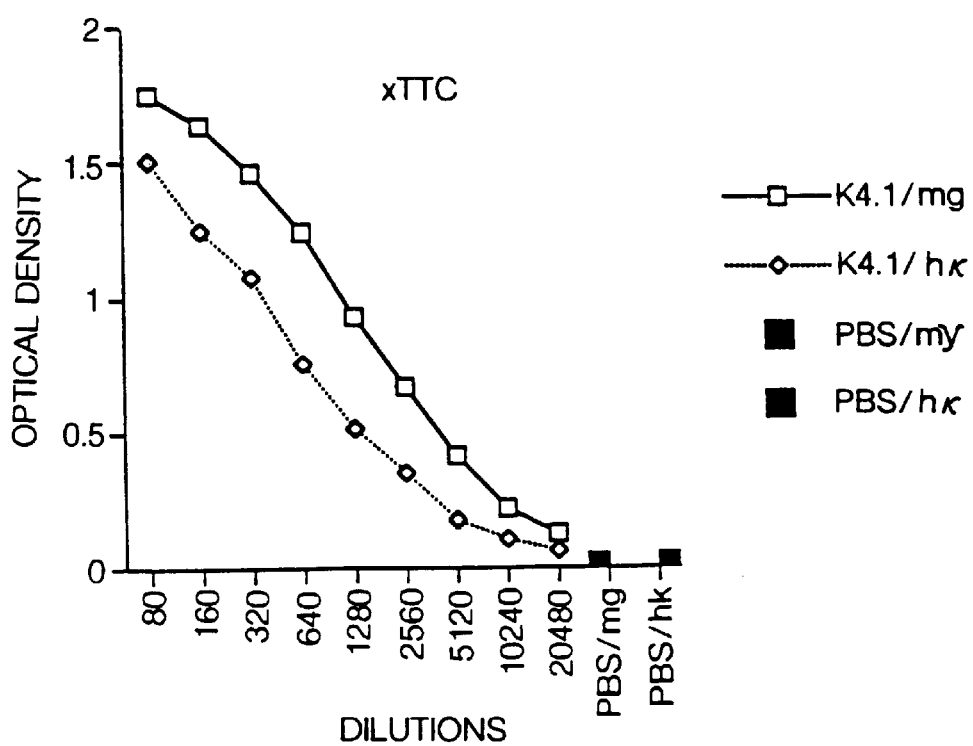
FIG. 14 is a titration curve with respect to the hybridoma supernatant from clone K4.1. This hybridoma clone is obtained from a xenomouse immunized with TTC and contains human kappa light chain and heavy chain having the murine γ constant region.

As shown in FIG. 13, clone D5.1 secretes fully human anti-TTC which is detectable using HRP-conjugated anti-human μ and HRP-conjugated antihuman kappa. FIG. 14 shows that clone K4.1 secretes anti-TTC which is immunoreactive with antimurine γ and antihuman kappa HRP-conjugated antibodies. Thus, clone K4.1 provides anti-TTC with human variable regions and a murine constant heavy chain γ region.

The antibodies secreted by D5.1 and K4.1 did not immunoreact in ELISAs using TNFα, IL-6, or IL-8 as immobilized antigen under conditions where positive controls (sera from xenomice immunized with TNFα, IL-6 and IL-8 respectively) showed positive ELISA results.

The affinity of the monoclonal antibodies secreted by K4.1 for TTC antigen was determined using commercially available reagents and instrumentation. BIAcore Instrument, CM5 sensor chips, surfactant P20 and the amine coupling kit were purchased from Pharmacia Biosensor (Piscataway, N.J.). TTC was immobilized at two levels of antigen density on the surface of the sensor chips according to the manufacturer's instructions. Briefly, after washing and equilibrating the instrument with buffer containing surfactant, the surfaces were activated and the TCC was immobilized.

For high antigen density, the surface was activated with 35 μl of equal volumes 0.1 M NHS and 0.1 M EDC injected across the surface followed by 30 μl of TTC fragment at 100 μg/ml in 10 mM sodium acetate buffer pH 5.0. The surface was blocked by injecting 35 μl 1 M ethanolamine and washed to remove noncovalently bound TCC using 5 μl 0.1 M HCl. The entire immobilization procedure was conducted with a continuous flow of buffer at 5 μl/min. This results in about 7500–8500 response units (RU) of TTC per chip. (1000 RU corresponds to about 1 ng of protein per $mm^2$.)

For chips with low antigen density, the procedure utilizes 15 μl rather than 30 μl of TTC, resulting in chips containing 550–950 RU.

Chips could be regenerated after use in single determinations by injecting 10 μl formal or $MgCl_2$.

Figure 15:
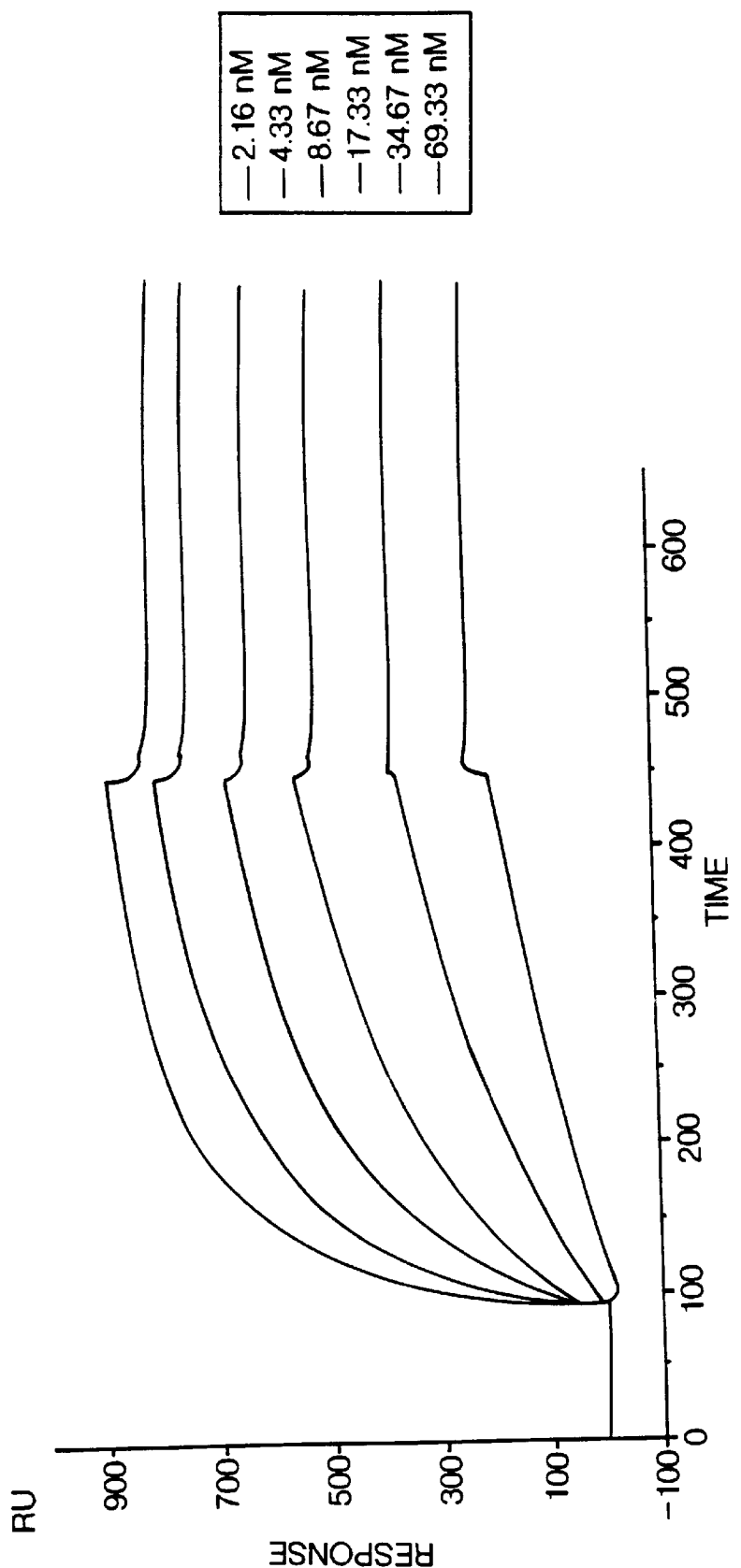
FIG. 15 shows binding curves for various concentrations of the K4.1 monoclonal antibody in a determination of the affinity of the monoclonal with its antigen in a BIAcore instrument.

The chips are used to determine binding affinities by determining $k_a$ and $k_b$ (the association and dissociation rate constants) for the antibody with respect to the immobilized TTC. The association rate constant is measured over six minutes at a flow rate of 5 μl/min. at different concentrations of K4.1 Mab in the range of 2.16 nm–69.33 rm. The dissociation rate constant is measured at a constant buffer flow rate of 5 μl/min after completion of the antibody injection. The raw data are graphed in FIG. 15 and the calculated results are shown in Table 1.

TABLE 1

Kinetic Constants of K4.1 Measured Using the BIAcore on Two Different Surfaces

| Immobilized tetanus toxinC | K4.1 conc. range nM | Association rate ka ($10^5$ $M^{-1}s^{-1}$) | Dissociation rate kd ($10^5s^{-1}$) | Binding constant KA ($M^{-1}$) = ka/kd | Dissociation constant KD (M) = kd/ka |
|---|---|---|---|---|---|
| 5931 RU | 4.3–34.7 | 6.47 ± 1.05 | 4.02 ± 1.42 | $1.6 \times 10^{10}$ | $0.62 \times 10^{-10}$ |
| 868 RU | 4.3–34.7 | 7.19 ± 2.18 | 2.02 ± 1.01 | $3.5 \times 10^{10}$ | $0.28 \times 10^{-10}$ |

As shown, the K4.1 antibody has a binding constant for TTC somewhat larger than $10^{10}$ 1/mol.

The complete nucleotide sequence of the cDNAs encoding the heavy and light chains of the K4.1 and D5.1 monoclonals were determined as shown in FIGS. 16–19. PolyA MRNA was isolated from about $10^6$ hybridoma cells and used to generate cDNA using random hexamers as primers. Portions of the product were amplified by PCR using the appropriate primers.

Both cell lines were known to provide human kappa light chains; for PCR amplification of light chain encoding cDNA, the primers used were HKP1 (5'-CTCTGTGACACTCTCCTGGGAGTT-3') (SEQ ID NO:1) for priming from the constant region terminus and two oligos, used in equal amounts to prime from the variable segments: B3 (5'-CCACCATCAACTGCAAGTCCAGCCA-3') (SEQ ID NO:2) and B2/B1 (5'-GAAACGACACTCACGCAGTCTCCAGC-3') (SEQ ID NO:3).

For amplification of the heavy chain from K4.1 (which contains the murine γ1 constant region), the primers were MG-24Vi for the human variable regions: 5'-CAGGTGCAGCTGGAGCAGTCiGG-3'(SEQ ID NO:4) which, with inosine as shown recognizes the human variable regions $V_{H1-2}$, $V_{H1-3}$, $V_{H4}$ and $V_{H6}$, and from the constant region MG-25 i.e., 5'-GCACACCGCTGGACAGGGATCCAiAGTTTC-3' (SEQ ID NO:5), which, containing inosine as shown recognizes murine γ1, γ2A, γ2B, and δ3.

For amplification of the heavy chain of the antibody derived from D5.1 (which contains the human μ constant region), MG-24VI was used to prime from the variable and μP1 (5'-TTTTCTTTGTTGCCGTTGGGGTGC-3') (SEQ ID NO:6) was used to prime from the constant region terminus.

Figure 16A:
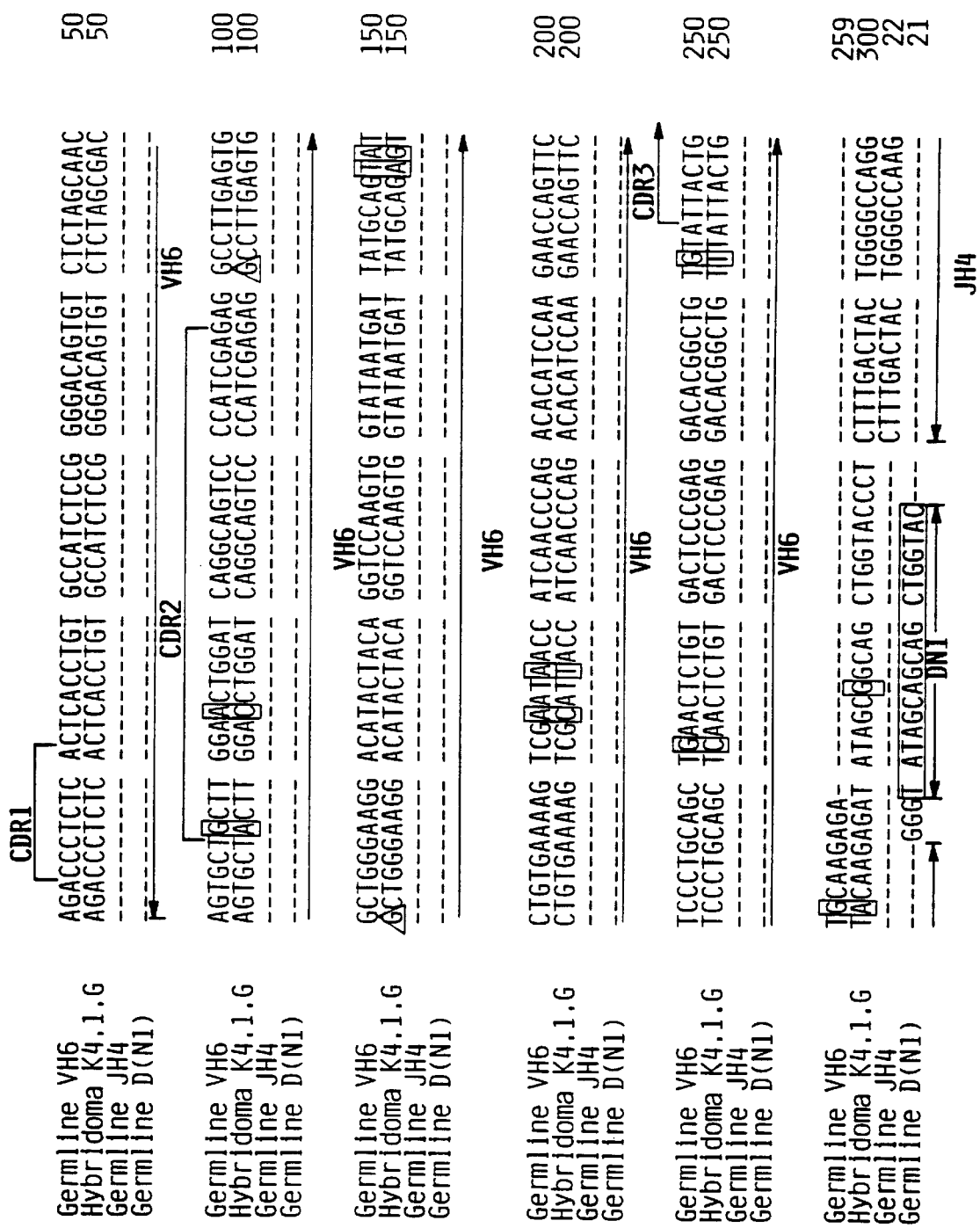
FIGS. 16A–16B show the complete nucleotide sequence of the heavy chain from the antibody secreted by K4.1.
Figure 16B:
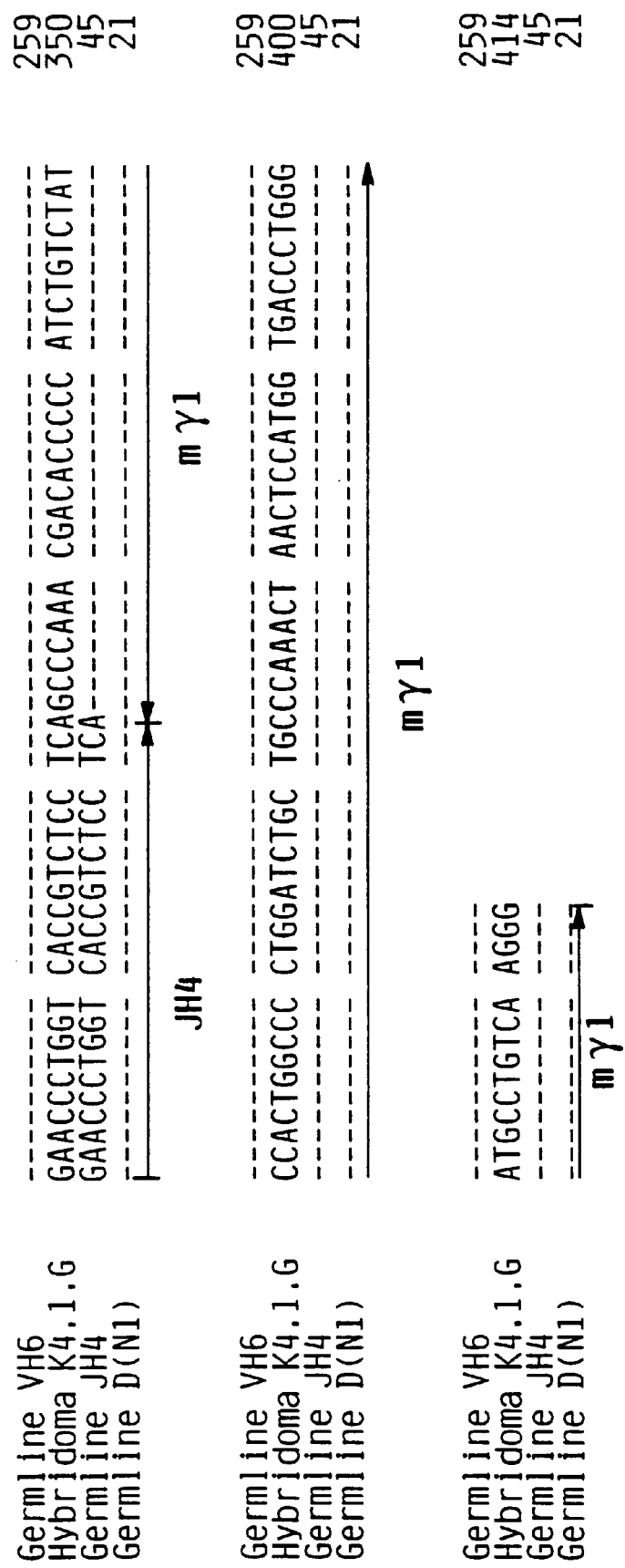

Turning first to the results shown in FIG. 16 representing the heavy chain of the Mab secreted by K4.1, the sequence shows the presence of the human variable segment VH6, the human diversity region DN1, and the human joining segment JH4 linked to the murine γ1 constant region. Nine base-pair mutations from the published germline sequence were present in the variable region, two of them within CDR2. One mutation was observed in the D segment. Three nongermline nucleotide additions were present in the $D_H$–$J_H$ junction.

Referring to FIG. 17 which shows the light chain of the K4.1 antibody, analysis shows the presence of the human kappa variable region B3 and joining region JK4. Eight nucleotides are missing from B3 at the $V_K$–$J_K$ junction and four mutations were found in the variable region. Five nongermline nucleotide additions were present at the $V_K$–$J_K$ junction.

Figure 18A:
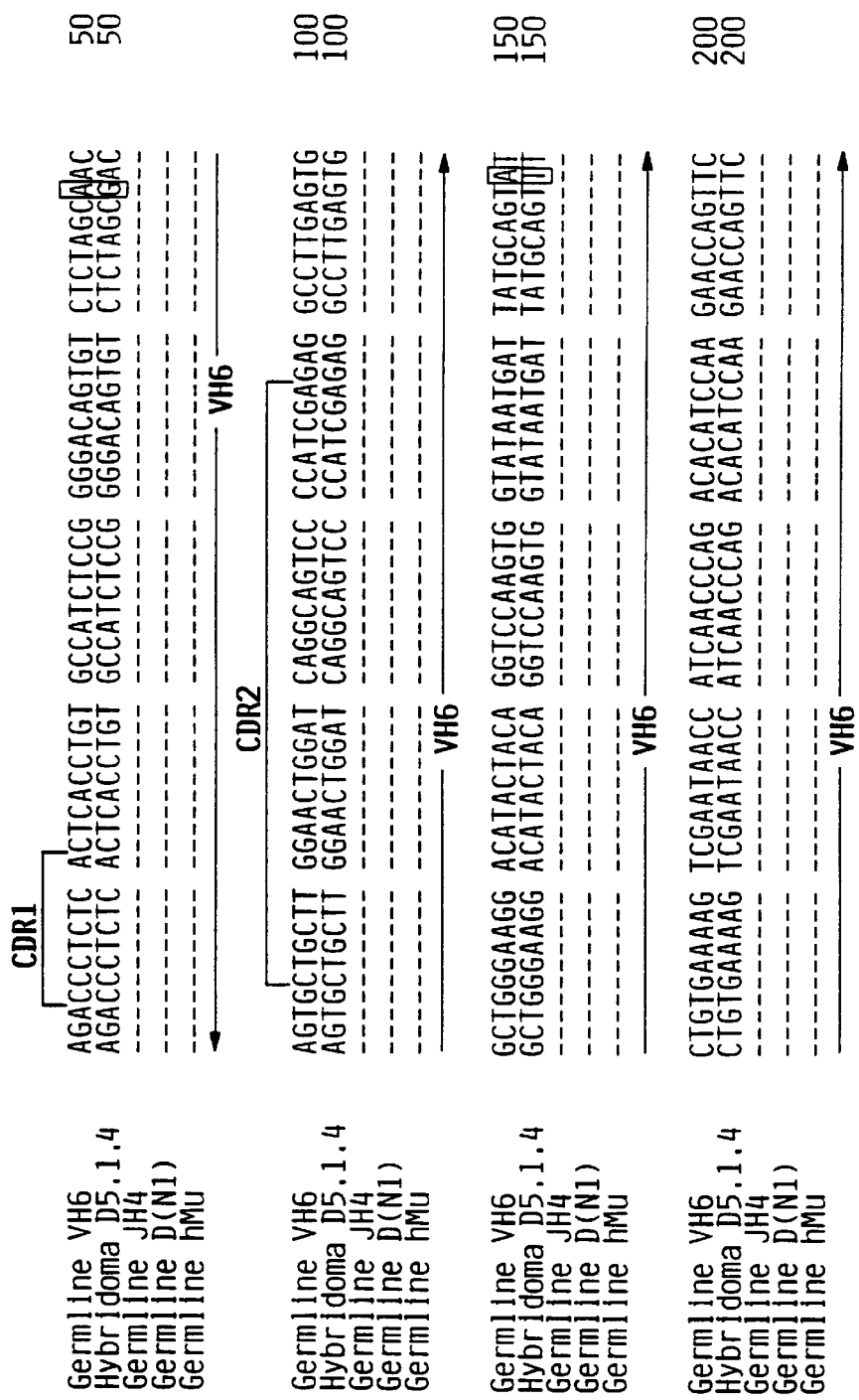

Referring now to FIG. 18 which sets forth the sequence for the heavy chain of the antibody secreted by clone D5.1, this shows the heavy chain is comprised of the human variable fragment VH6, the human diversity region DN1 and the human joining segment JH4 linked to the human μ constant region. There were two base-pair mutations from the germline sequence in the variable region, neither within the CDRs. Two additional mutations were in the D segment and six nongermline nucleotide additions were present at the $D_H$–$J_H$ junction.

Figure 19A:
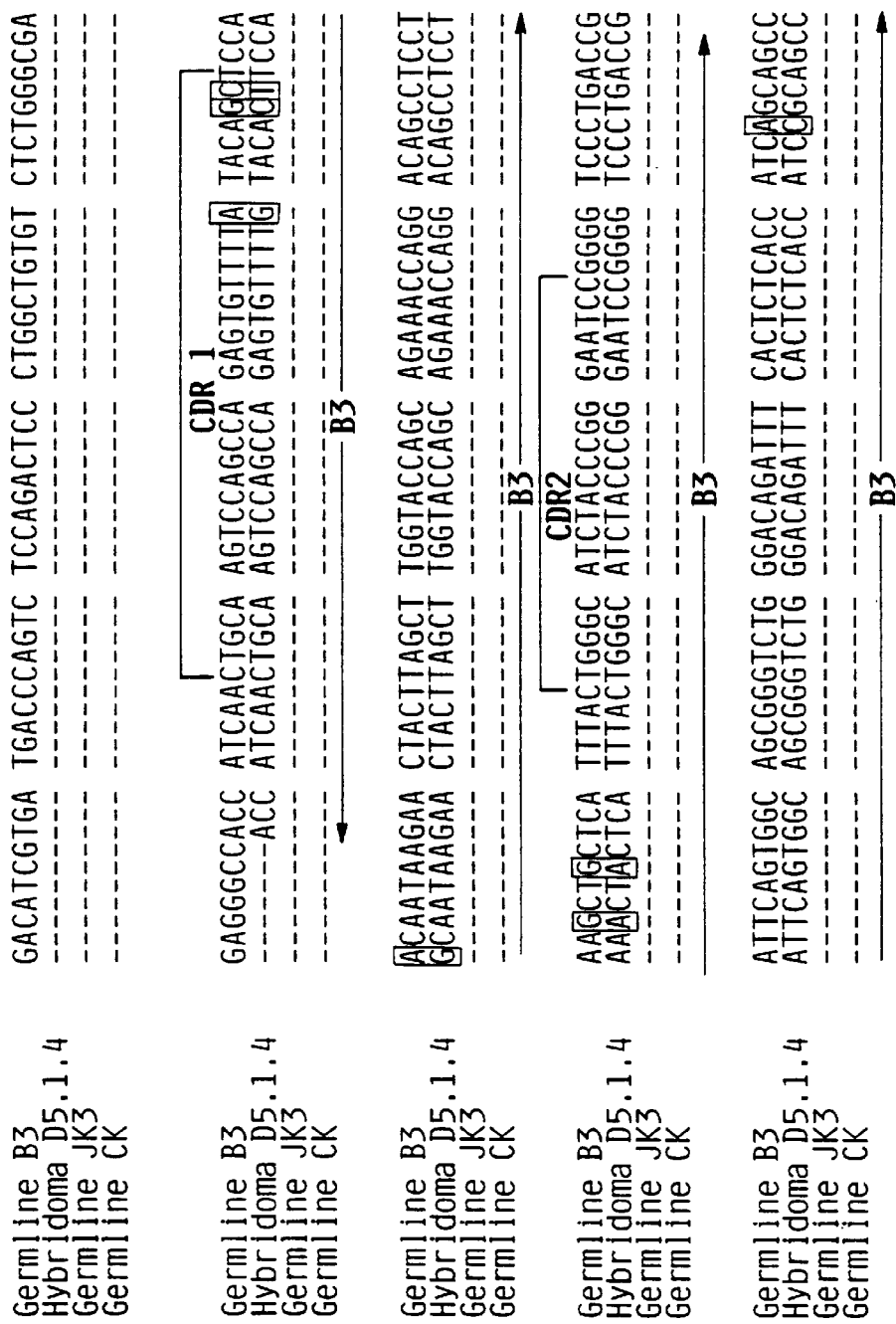
Figure 19B:
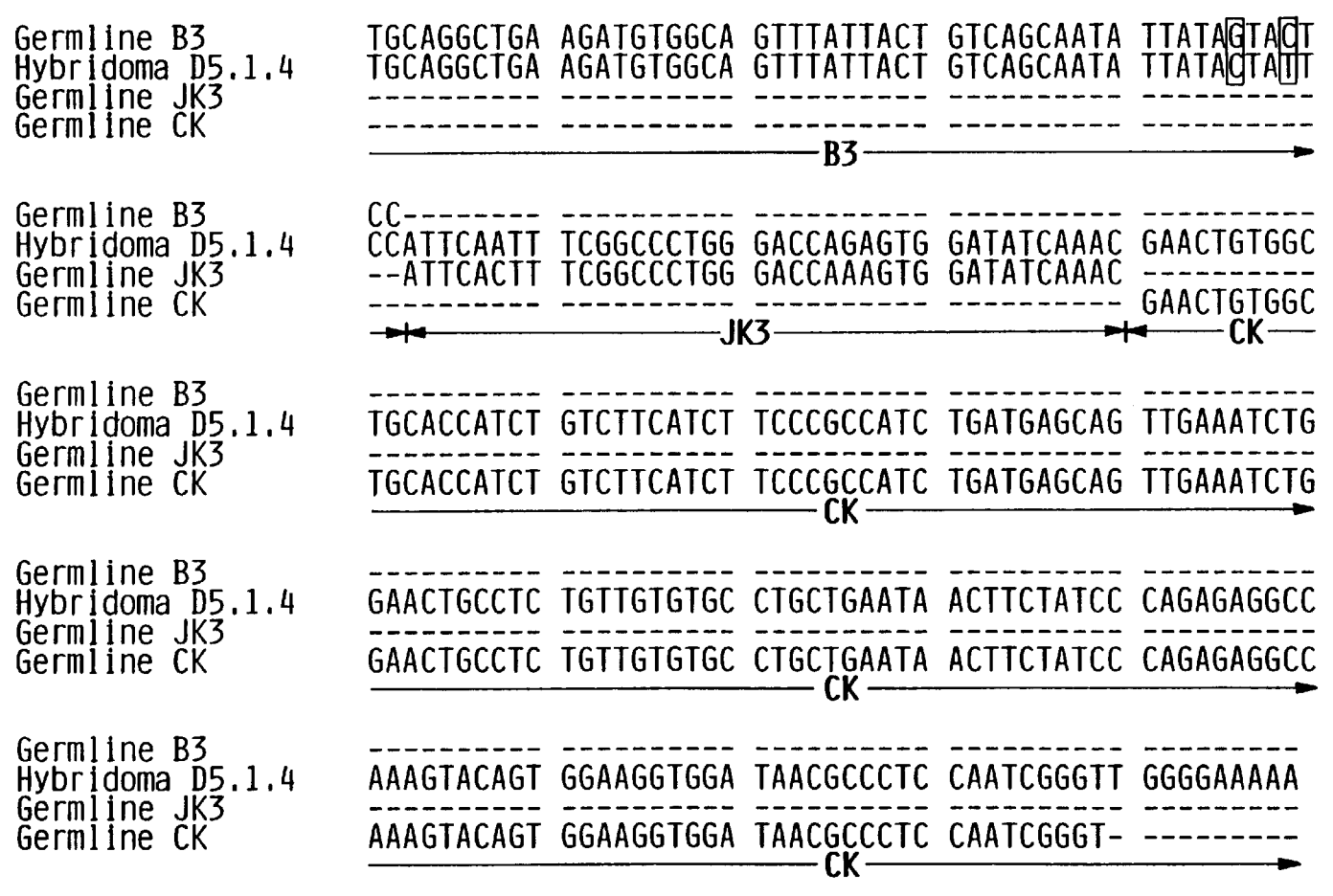

Finally, referring to FIG. 19 which presents the light chain of the antibody secreted by D5.1, the human kappa variable region B3 and human kappa joining region JK3 are shown. There are nine base-pair differences from the germline sequences, three falling within CDR1.

What is claimed is:

1. A method for producing a transgenic mouse wherein the germ cells comprise at least one inactivated endogenous immunoglobulin heavy chain locus in which all of the J segment genes are deleted to prevent rearrangement of the locus and to prevent formation of a transcript of a rearranged locus and the expression of an endogenous immunoglobulin heavy chain from the inactivated locus, said method comprising the steps of:

(a) deleting the J segment genes from at least one endogenous heavy chain locus in a mouse embryonic stem cell to prevent rearrangement of said locus and to prevent formation of a transcript of a rearranged immunoglobulin heavy chain locus, the deletion being effected by a targeting vector comprising a gene encoding a selectable marker; and (b) producing from the embryonic stem cell a transgenic mouse whose germ cells comprise at least one immunoglobulin heavy chain locus in which all of the J segment genes are deleted.

2. A method for producing a transgenic mouse and its progeny, wherein the somatic and germ cells comprise at least one inactivated endogenous immunoglobulin heavy chain locus in which all of the J segment genes are deleted to prevent rearrangement of the locus and to prevent formation of a transcript of a rearranged locus and the expression of an endogenous immunoglobulin heavy chain from the inactivated locus, said method comprising the steps of:

(a) deleting the J segment genes from at least one endogenous heavy chain locus in a mouse embryonic stem cell to prevent rearrangement of the locus and to prevent formation of a transcript of a rearranged immunoglobulin heavy chain locus, the deletion being effected by a targeting vector comprising a gene encoding a selectable marker;

(b) producing from the embryonic stem cell a transgenic mouse whose germ cells comprise at least one immunoglobulin heavy chain locus in which all of the J segment genes are deleted, and (c) breeding the transgenic mouse as needed to produce a transgenic mouse and its progeny whose somatic and germ cells comprise at least one inactivated endogenous immunoglobulin heavy chain locus in which all of the J segment genes are deleted.

3. The method according to claim 1 or claim 2, wherein the gene encoding a selectable marker is a neomycin resistance gene.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: unknown
      (D) TOPOLOGY: unknown (ii) MOLECULE TYPE: DNA (genomic)

(xi) SEQUENCE DESCRIPTION: SEQ ID NO:1:

CTCTGTGACA CTCTCCTGGG AGTT                                 24

(2) INFORMATION FOR SEQ ID NO:2:

(i) SEQUENCE CHARACTERISTICS:
      (A) LENGTH: 25 base pairs
      (B) TYPE: nucleic acid
      (C) STRANDEDNESS: unknown
      (D) TOPOLOGY: unknown (ii) MOLECULE TYPE: DNA (genomic)

(xi) SEQUENCE DESCRIPTION: SEQ ID NO:2:

CCACCATCAA CTGCAAGTCC AGCCA                                25

(2) INFORMATION FOR SEQ ID NO:3:

(i) SEQUENCE CHARACTERISTICS:
      (A) LENGTH: 26 base pairs
      (B) TYPE: nucleic acid
      (C) STRANDEDNESS: unknown
      (D) TOPOLOGY: unknown (ii) MOLECULE TYPE: DNA (genomic)

(xi) SEQUENCE DESCRIPTION: SEQ ID NO:3:

GAAACGACAC TCACGCAGTC TCCAGC                               26

(2) INFORMATION FOR SEQ ID NO:4:

(i) SEQUENCE CHARACTERISTICS:
      (A) LENGTH: 23 base pairs
      (B) TYPE: nucleic acid
      (C) STRANDEDNESS: unknown

```
            (D) TOPOLOGY: unknown (ii) MOLECULE TYPE: DNA (genomic)

(ix) FEATURE:
            (A) NAME/KEY: misc_feature
            (B) LOCATION: 21
            (D) OTHER INFORMATION: /note= "Where N=i=inosine"

(xi) SEQUENCE DESCRIPTION: SEQ ID NO:4:

CAGGTGCAGC TGGAGCAGTC NGG                                            23

(2) INFORMATION FOR SEQ ID NO:5:

(i) SEQUENCE CHARACTERISTICS:
            (A) LENGTH: 30 base pairs
            (B) TYPE: nucleic acid
            (C) STRANDEDNESS: unknown
            (D) TOPOLOGY: unknown (ii) MOLECULE TYPE: DNA (genomic)

(ix) FEATURE:
            (A) NAME/KEY: misc_feature
            (B) LOCATION: 24
            (D) OTHER INFORMATION: /note= "Where N=i=inosine"

(xi) SEQUENCE DESCRIPTION: SEQ ID NO:5:

GCACACCGCT GGACAGGGAT CCANAGTTTC                                     30

(2) INFORMATION FOR SEQ ID NO:6:

(i) SEQUENCE CHARACTERISTICS:
            (A) LENGTH: 24 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:6:

TTTTCTTTGT TGCCGTTGGG GTGC                                           24
```